United States Patent
Wallace et al.

(10) Patent No.: US 10,278,774 B2
(45) Date of Patent: May 7, 2019

(54) SELECTIVELY EXPANDABLE OPERATIVE ELEMENT SUPPORT STRUCTURE AND METHODS OF USE

(75) Inventors: Michael P. Wallace, Pleasanton, CA (US); Robert Garabedian, Sunnyvale, CA (US); David S. Utley, Redwood City, CA (US); Brent C. Gerberding, San Jose, CA (US); John de Csepel, New York, NY (US)

(73) Assignee: COVIDIEN LP, Mansfield, MA (US)

( * ) Notice: Subject to any disclaimer, the term of this patent is extended or adjusted under 35 U.S.C. 154(b) by 1489 days.

(21) Appl. No.: 13/051,738

(22) Filed: Mar. 18, 2011

(65) Prior Publication Data

US 2012/0239028 A1 Sep. 20, 2012

(51) Int. Cl.
*A61B 18/12* (2006.01)
*A61B 18/14* (2006.01)
(Continued)

(52) U.S. Cl.
CPC .......... *A61B 18/1492* (2013.01); *A61B 18/06* (2013.01); *A61B 18/082* (2013.01); *A61B 18/24* (2013.01);
(Continued)

(58) Field of Classification Search
CPC .......... A61B 2018/00059; A61B 2018/00214; A61B 2018/00255; A61B 2018/00488;
(Continued)

(56) References Cited

U.S. PATENT DOCUMENTS 552,832 A 1/1896 Fort
3,901,241 A 8/1975 Allen, Jr.
(Continued)

FOREIGN PATENT DOCUMENTS

CN 101495048 A 7/2009
CN 202637109 U 1/2013
(Continued)

OTHER PUBLICATIONS

Castell, D.O. Gastroesophageal Reflux Disease: Current Strategies for Patient Management. Arch Fam Med. 1996; 5(4):221-227.
(Continued)

*Primary Examiner* — Daniel W Fowler

(57) ABSTRACT

In one embodiment, a device is provided including an expandable support member having a first portion and a second portion is provided. The first portion is adapted to have a smaller expansion index than the second portion. A therapeutic or diagnostic instrument is supported, at least in part, by the expandable support member first portion. In another embodiment, the support member is adapted for non-uniform expansion of the first and second portions. There are also described methods of forming therapeutic devices. There are also described methods of providing therapy to tissue in a body by positioning a device in proximity to tissue in a body selected to receive therapy. Next, the expandable support member second portion is expanded until the instrument is at a therapeutic position relative to the tissue in a body selected to receive therapy. Thereafter, therapy or diagnosis is provided to the selected tissue using the device.

33 Claims, 9 Drawing Sheets

(51) Int. Cl.
   *A61B 18/00* (2006.01)
   *A61N 7/02* (2006.01)
   *A61B 18/06* (2006.01)
   *A61B 18/08* (2006.01)
   *A61B 18/24* (2006.01)
   *A61B 18/02* (2006.01)
   *A61B 18/18* (2006.01)

(52) U.S. Cl.
   CPC .......... *A61B 2018/0016* (2013.01); *A61B 2018/0022* (2013.01); *A61B 2018/00488* (2013.01); *A61B 2018/00577* (2013.01); *A61B 2018/0212* (2013.01); *A61B 2018/1497* (2013.01); *A61B 2018/1861* (2013.01); *A61N 7/022* (2013.01)

(58) Field of Classification Search
   CPC ........ A61B 2018/00589; A61B 2018/00577; A61B 2018/00261; A61B 18/0206; A61B 18/0218; A61B 18/04; A61B 18/1815; A61B 18/1482; A61B 18/14; A61B 17/12136
   USPC .................................................. 606/20–52
   See application file for complete search history.

(56) References Cited

U.S. PATENT DOCUMENTS

| | | |
|---|---|---|
| 3,924,628 A | 12/1975 | Droegemueller et al. |
| 4,011,872 A | 3/1977 | Komiya |
| 4,304,239 A | 12/1981 | Perlin |
| 4,311,154 A | 1/1982 | Sterzer et al. |
| 4,407,298 A | 10/1983 | Lentz et al. |
| 4,411,266 A | 10/1983 | Cosman |
| 4,532,924 A | 8/1985 | Auth et al. |
| 4,565,200 A | 1/1986 | Cosman |
| 4,640,298 A | 2/1987 | Pless et al. |
| 4,658,836 A | 4/1987 | Turner |
| 4,662,383 A | 5/1987 | Sogawa et al. |
| 4,674,481 A | 6/1987 | Boddie, Jr. et al. |
| 4,676,258 A | 6/1987 | Inokuchi et al. |
| 4,709,698 A | 12/1987 | Johnston et al. |
| 4,765,331 A | 8/1988 | Petruzzi et al. |
| 4,776,349 A | 10/1988 | Nashef et al. |
| 4,860,744 A | 8/1989 | Johnson et al. |
| 4,887,614 A | 12/1989 | Shirakami et al. |
| 4,895,138 A | 1/1990 | Yabe |
| 4,907,589 A | 3/1990 | Cosman |
| 4,930,521 A | 6/1990 | Metzger et al. |
| 4,943,290 A | 7/1990 | Rexroth et al. |
| 4,947,842 A | 8/1990 | Marchosky et al. |
| 4,949,147 A | 8/1990 | Bacuvier |
| 4,955,377 A | 9/1990 | Lennox et al. |
| 4,966,597 A | 10/1990 | Cosman |
| 4,969,890 A | 11/1990 | Sugita et al. |
| 4,976,711 A | 12/1990 | Parins et al. |
| 4,979,948 A | 12/1990 | Geddes et al. |
| 4,998,539 A | 3/1991 | Delsanti |
| 5,006,119 A | 4/1991 | Acker et al. |
| 5,010,895 A | 4/1991 | Maurer et al. |
| 5,019,075 A | 5/1991 | Spears et al. |
| 5,035,696 A | 7/1991 | Rydell |
| 5,045,056 A | 9/1991 | Behl |
| 5,046,512 A | 9/1991 | Murchie |
| 5,047,028 A | 9/1991 | Qian |
| 5,056,532 A | 10/1991 | Hull et al. |
| 5,057,107 A | 10/1991 | Parins et al. |
| 5,078,717 A | 1/1992 | Parins et al. |
| 5,083,565 A | 1/1992 | Parins |
| 5,084,044 A | 1/1992 | Quint |
| 5,088,979 A | 2/1992 | Filipi et al. |
| 5,100,423 A | 3/1992 | Fearnot |
| 5,106,360 A | 4/1992 | Ishiwara et al. |
| 5,117,828 A | 6/1992 | Metzger et al. |
| 5,122,137 A | 6/1992 | Lennox |
| 5,125,928 A | 6/1992 | Parins et al. |
| 5,151,100 A | 9/1992 | Abele et al. |
| 5,156,151 A | 10/1992 | Imran |
| 5,163,938 A | 11/1992 | Kambara et al. |
| 5,171,299 A | 12/1992 | Heitzmann et al. |
| 5,190,541 A | 3/1993 | Abele et al. |
| 5,197,963 A | 3/1993 | Parins |
| 5,197,964 A | 3/1993 | Parins |
| 5,215,103 A | 6/1993 | Desai |
| 5,236,413 A | 8/1993 | Fiering |
| 5,242,441 A | 9/1993 | Avitall |
| 5,255,679 A | 10/1993 | Imran |
| 5,256,138 A | 10/1993 | Vurek et al. |
| 5,257,451 A | 11/1993 | Edwards et al. |
| 5,263,493 A | 11/1993 | Avitall |
| 5,275,162 A | 1/1994 | Edwards et al. |
| 5,275,169 A | 1/1994 | Afromowitz et al. |
| 5,277,201 A | 1/1994 | Stern |
| 5,281,216 A | 1/1994 | Klicek |
| 5,281,217 A | 1/1994 | Edwards et al. |
| 5,281,218 A | 1/1994 | Imran |
| 5,290,286 A | 3/1994 | Parins |
| 5,292,321 A | 3/1994 | Lee |
| 5,293,869 A | 3/1994 | Edwards et al. |
| 5,309,910 A | 5/1994 | Edwards et al. |
| 5,313,943 A | 5/1994 | Houser et al. |
| 5,314,438 A | 5/1994 | Shturman |
| 5,314,466 A | 5/1994 | Stern et al. |
| 5,316,020 A | 5/1994 | Truffer |
| 5,324,284 A | 6/1994 | Imran |
| 5,328,467 A | 7/1994 | Edwards et al. |
| 5,336,222 A | 8/1994 | Durgin, Jr. et al. |
| 5,345,936 A | 9/1994 | Pomeranz et al. |
| 5,348,554 A | 9/1994 | Imran et al. |
| 5,363,861 A | 11/1994 | Edwards et al. |
| 5,365,926 A | 11/1994 | Desai |
| 5,366,490 A | 11/1994 | Edwards et al. |
| 5,368,557 A | 11/1994 | Nita et al. |
| 5,368,592 A | 11/1994 | Stern et al. |
| 5,370,675 A | 12/1994 | Edwards et al. |
| 5,370,678 A | 12/1994 | Edwards et al. |
| 5,372,138 A | 12/1994 | Crowley et al. |
| 5,375,594 A | 12/1994 | Cueva |
| 5,383,876 A | 1/1995 | Nardella |
| 5,383,917 A | 1/1995 | Desai et al. |
| 5,385,544 A | 1/1995 | Edwards et al. |
| 5,397,339 A | 3/1995 | Desai |
| 5,398,683 A | 3/1995 | Edwards et al. |
| 5,401,272 A | 3/1995 | Perkins |
| 5,403,311 A | 4/1995 | Abele et al. |
| 5,409,453 A | 4/1995 | Lundquist et al. |
| 5,409,483 A | 4/1995 | Campbell et al. |
| 5,411,025 A | 5/1995 | Webster, Jr. |
| 5,413,573 A | 5/1995 | Koivukangas |
| 5,415,657 A | 5/1995 | Taymor-Luia |
| 5,421,819 A | 6/1995 | Edwards et al. |
| 5,423,808 A | 6/1995 | Edwards et al. |
| 5,423,811 A | 6/1995 | Imran et al. |
| 5,423,812 A | 6/1995 | Ellman et al. |
| 5,425,704 A | 6/1995 | Sakurai et al. |
| 5,428,658 A | 6/1995 | Oettinger et al. |
| 5,433,739 A | 7/1995 | Sluijter et al. |
| 5,435,805 A | 7/1995 | Edwards |
| 5,441,499 A | 8/1995 | Fritzsch |
| 5,443,470 A | 8/1995 | Stern et al. |
| 5,454,782 A | 10/1995 | Perkins |
| 5,454,809 A | 10/1995 | Janssen |
| 5,456,662 A | 10/1995 | Edwards et al. |
| 5,456,682 A | 10/1995 | Edwards et al. |
| 5,458,571 A | 10/1995 | Lampropoulos et al. |
| 5,458,596 A | 10/1995 | Lax et al. |
| 5,458,597 A | 10/1995 | Edwards et al. |
| 5,462,545 A | 10/1995 | Wang et al. |
| 5,465,717 A | 11/1995 | Imran et al. |
| 5,470,308 A | 11/1995 | Edwards et al. |
| 5,471,982 A | 12/1995 | Edwards et al. |
| 5,472,441 A | 12/1995 | Edwards et al. |
| 5,484,400 A | 1/1996 | Edwards et al. |

(56) References Cited

U.S. PATENT DOCUMENTS

| | | |
|---|---|---|
| 5,486,161 A | 1/1996 | Lax et al. |
| 5,490,984 A | 2/1996 | Freed |
| 5,496,271 A | 3/1996 | Burton et al. |
| 5,496,311 A | 3/1996 | Abele et al. |
| 5,500,012 A | 3/1996 | Brucker et al. |
| 5,505,728 A | 4/1996 | Ellman et al. |
| 5,505,730 A | 4/1996 | Edwards |
| 5,507,743 A | 4/1996 | Edwards et al. |
| 5,509,419 A | 4/1996 | Edwards et al. |
| 5,514,130 A | 5/1996 | Baker |
| 5,514,131 A | 5/1996 | Edwards et al. |
| 5,517,989 A | 5/1996 | Frisbie et al. |
| 5,520,684 A | 5/1996 | Imran |
| 5,522,815 A | 6/1996 | Burgin, Jr. et al. |
| 5,524,622 A | 6/1996 | Wilson |
| 5,531,676 A | 7/1996 | Edwards et al. |
| 5,531,677 A | 7/1996 | Lundquist et al. |
| 5,533,958 A | 7/1996 | Wilk |
| 5,536,240 A | 7/1996 | Edwards et al. |
| 5,536,267 A | 7/1996 | Edwards et al. |
| 5,540,655 A | 7/1996 | Edwards et al. |
| 5,540,679 A | 7/1996 | Fram et al. |
| 5,542,916 A | 8/1996 | Hirsch et al. |
| 5,542,928 A | 8/1996 | Evans et al. |
| 5,549,644 A | 8/1996 | Lundquist et al. |
| 5,549,661 A | 8/1996 | Korkis et al. |
| RE35,330 E | 9/1996 | Malone et al. |
| 5,554,110 A | 9/1996 | Edwards et al. |
| 5,556,377 A | 9/1996 | Rosen et al. |
| 5,558,672 A | 9/1996 | Edwards et al. |
| 5,558,673 A | 9/1996 | Edwards et al. |
| 5,562,720 A | 10/1996 | Stern et al. |
| 5,566,221 A | 10/1996 | Smith et al. |
| 5,569,241 A | 10/1996 | Edwards |
| 5,571,116 A | 11/1996 | Bolanos et al. |
| 5,578,007 A | 11/1996 | Imran |
| 5,588,432 A | 12/1996 | Crowley |
| 5,588,960 A | 12/1996 | Edwards et al. |
| 5,591,195 A | 1/1997 | Taheri et al. |
| 5,599,345 A | 2/1997 | Edwards et al. |
| 5,609,151 A | 3/1997 | Muller et al. |
| 5,621,780 A | 4/1997 | Smith et al. |
| 5,624,439 A | 4/1997 | Edwards et al. |
| 5,651,780 A | 7/1997 | Jackson et al. |
| 5,651,788 A | 7/1997 | Fleischer et al. |
| 5,658,278 A | 8/1997 | Imran et al. |
| 5,672,153 A | 9/1997 | Lax et al. |
| 5,676,674 A | 10/1997 | Bolanos et al. |
| 5,688,266 A | 11/1997 | Edwards et al. |
| 5,688,490 A | 11/1997 | Tournier et al. |
| 5,702,438 A | 12/1997 | Avitall |
| 5,709,224 A | 1/1998 | Behl et al. |
| 5,713,942 A | 2/1998 | Stern et al. |
| 5,716,410 A | 2/1998 | Wang et al. |
| 5,720,293 A | 2/1998 | Quinn et al. |
| 5,730,128 A | 3/1998 | Pomeranz et al. |
| 5,732,698 A | 3/1998 | Swanson et al. |
| 5,738,096 A | 4/1998 | Ben-Haim |
| 5,748,699 A | 5/1998 | Smith |
| 5,769,846 A | 6/1998 | Edwards et al. |
| 5,769,880 A * | 6/1998 | Truckai et al. ............... 607/101 |
| 5,772,681 A * | 6/1998 | Leoni ............................ 606/192 |
| 5,779,698 A | 7/1998 | Clayman et al. |
| 5,797,835 A | 8/1998 | Green |
| 5,797,903 A | 8/1998 | Swanson et al. |
| 5,800,334 A | 9/1998 | Wilk |
| 5,800,429 A | 9/1998 | Edwards |
| 5,807,261 A | 9/1998 | Benaron et al. |
| 5,820,629 A | 10/1998 | Cox |
| 5,823,197 A | 10/1998 | Edwards |
| 5,823,955 A | 10/1998 | Kuck et al. |
| 5,827,273 A | 10/1998 | Edwards |
| 5,830,129 A | 11/1998 | Baer et al. |
| 5,830,213 A | 11/1998 | Panescu et al. |
| 5,833,688 A | 11/1998 | Sieben et al. |
| 5,836,874 A | 11/1998 | Swanson et al. |
| 5,842,984 A | 12/1998 | Avitall |
| 5,846,196 A | 12/1998 | Siekmeyer et al. |
| 5,860,974 A | 1/1999 | Abele |
| 5,861,036 A | 1/1999 | Godin |
| 5,863,291 A | 1/1999 | Schaer |
| 5,871,483 A | 2/1999 | Jackson et al. |
| 5,876,340 A | 3/1999 | Tu et al. |
| 5,888,743 A | 3/1999 | Das |
| 5,891,134 A | 4/1999 | Goble et al. |
| 5,895,355 A | 4/1999 | Schaer |
| 5,902,263 A | 5/1999 | Patterson et al. |
| 5,904,711 A | 5/1999 | Flom et al. |
| 5,925,044 A | 7/1999 | Hofmann et al. |
| 5,938,694 A | 8/1999 | Jaraczewski et al. |
| 5,964,755 A | 10/1999 | Edwards |
| 5,976,129 A | 11/1999 | Desai |
| 5,984,861 A | 11/1999 | Crowley |
| 5,991,650 A * | 11/1999 | Swanson et al. ............. 600/374 |
| 5,997,534 A | 12/1999 | Tu et al. |
| 6,006,755 A | 12/1999 | Edwards |
| 6,010,511 A | 1/2000 | Murphy |
| 6,012,457 A | 1/2000 | Lesh |
| 6,016,437 A | 1/2000 | Tu et al. |
| 6,023,638 A | 2/2000 | Swanson et al. |
| 6,027,499 A | 2/2000 | Johnston et al. |
| 6,033,397 A | 3/2000 | Laufer et al. |
| 6,039,701 A | 3/2000 | Sliwa et al. |
| 6,041,260 A | 3/2000 | Stern et al. |
| 6,044,846 A | 4/2000 | Edwards |
| 6,053,172 A | 4/2000 | Hovda et al. |
| 6,053,913 A | 4/2000 | Tu et al. |
| 6,056,744 A | 5/2000 | Edwards |
| 6,059,719 A | 5/2000 | Yamamoto et al. |
| 6,068,629 A | 5/2000 | Haissaguerre et al. |
| 6,071,277 A | 6/2000 | Farley et al. |
| 6,073,052 A | 6/2000 | Zelickson et al. |
| 6,086,558 A | 7/2000 | Bower et al. |
| 6,091,993 A * | 7/2000 | Bouchier et al. ............... 607/98 |
| 6,091,995 A | 7/2000 | Ingle et al. |
| 6,092,528 A | 7/2000 | Edwards |
| 6,095,966 A | 8/2000 | Chornenky et al. |
| 6,096,054 A | 8/2000 | Wyzgala et al. |
| 6,102,908 A | 8/2000 | Tu et al. |
| 6,112,123 A | 8/2000 | Kelleher et al. |
| 6,120,434 A | 9/2000 | Kimura et al. |
| 6,123,703 A | 9/2000 | Tu et al. |
| 6,123,718 A | 9/2000 | Tu et al. |
| 6,138,046 A | 10/2000 | Dalton |
| 6,142,993 A * | 11/2000 | Whayne et al. ............... 606/41 |
| 6,142,994 A | 11/2000 | Swanson et al. |
| 6,146,149 A | 11/2000 | Daound |
| 6,149,647 A | 11/2000 | Tu et al. |
| 6,162,237 A | 12/2000 | Chan |
| 6,163,716 A * | 12/2000 | Edwards et al. ............. 600/374 |
| 6,179,836 B1 | 1/2001 | Eggers et al. |
| 6,182,666 B1 | 2/2001 | Dobak, III |
| 6,183,468 B1 | 2/2001 | Swanson et al. |
| 6,197,022 B1 | 3/2001 | Baker |
| 6,237,355 B1 | 5/2001 | Li |
| 6,238,392 B1 | 5/2001 | Long |
| 6,245,065 B1 | 6/2001 | Panescu et al. |
| 6,254,598 B1 | 7/2001 | Edwards et al. |
| 6,258,087 B1 | 7/2001 | Edwards et al. |
| 6,273,886 B1* | 8/2001 | Edwards ................ A61B 18/12 |
| | | 606/34 |
| 6,302,904 B1* | 10/2001 | Wallsten et al. ............. 607/105 |
| 6,321,121 B1 | 11/2001 | Zelickson et al. |
| 6,325,798 B1 | 12/2001 | Edwards et al. |
| 6,325,800 B1 | 12/2001 | Durgin et al. |
| 6,338,726 B1 | 1/2002 | Edwards et al. |
| 6,355,031 B1 | 3/2002 | Edwards et al. |
| 6,355,032 B1 | 3/2002 | Hovda et al. |
| 6,358,245 B1 | 3/2002 | Edwards et al. |
| 6,363,937 B1 | 4/2002 | Hovda et al. |
| 6,383,181 B1 | 5/2002 | Johnston et al. |
| 6,394,949 B1 | 5/2002 | Crowley et al. |
| 6,402,744 B2 | 6/2002 | Edwards et al. |
| 6,405,732 B1 | 6/2002 | Edwards et al. |

(56) References Cited

U.S. PATENT DOCUMENTS

| | | |
|---|---|---|
| 6,409,723 B1 | 6/2002 | Edwards |
| 6,415,016 B1 | 7/2002 | Chornenky et al. |
| 6,416,511 B1 | 7/2002 | Lesh et al. |
| 6,423,058 B1 | 7/2002 | Edwards et al. |
| 6,425,877 B1 | 7/2002 | Edwards |
| 6,428,536 B2 | 8/2002 | Panescu et al. |
| 6,432,104 B1 | 8/2002 | Durgin et al. |
| 6,440,128 B1 | 8/2002 | Edwards et al. |
| 6,448,658 B2 | 9/2002 | Takata et al. |
| 6,451,014 B1 | 9/2002 | Wakikaido et al. |
| 6,454,790 B1 | 9/2002 | Neuberger et al. |
| 6,464,697 B1 | 10/2002 | Edwards et al. |
| 6,468,272 B1 | 10/2002 | Koblish et al. |
| 6,514,246 B1 | 2/2003 | Swanson et al. |
| 6,514,249 B1 * | 2/2003 | Maguire et al. ............... 606/41 |
| 6,535,768 B1 | 3/2003 | Baker et al. |
| 6,544,224 B1 * | 4/2003 | Steese-Bradley ........ 604/103.06 |
| 6,544,226 B1 | 4/2003 | Gaiser et al. |
| 6,547,776 B1 | 4/2003 | Gaiser et al. |
| 6,547,787 B1 | 4/2003 | Altman et al. |
| 6,551,302 B1 | 4/2003 | Rosinko et al. |
| 6,551,310 B1 | 4/2003 | Ganz et al. |
| 6,551,315 B2 | 4/2003 | Kortenbach et al. |
| 6,558,385 B1 * | 5/2003 | McClurken et al. ........... 606/50 |
| 6,562,034 B2 | 5/2003 | Edwards et al. |
| 6,572,578 B1 | 6/2003 | Blanchard |
| 6,572,610 B2 | 6/2003 | Kovalcheck et al. |
| 6,572,612 B2 * | 6/2003 | Stewart et al. ................ 606/41 |
| 6,572,639 B1 | 6/2003 | Ingle et al. |
| 6,575,966 B2 | 6/2003 | Lane et al. |
| 6,589,238 B2 * | 7/2003 | Edwards et al. ............... 606/41 |
| 6,613,047 B2 | 9/2003 | Edwards |
| 6,641,581 B2 | 11/2003 | Muzzammel |
| 6,663,626 B2 | 12/2003 | Truckai et al. |
| 6,673,070 B2 | 1/2004 | Edwards et al. |
| 6,682,528 B2 | 1/2004 | Frazier et al. |
| 6,689,130 B2 | 2/2004 | Arail et al. |
| 6,695,764 B2 | 2/2004 | Silverman et al. |
| 6,712,074 B2 | 3/2004 | Edwards et al. |
| 6,712,814 B2 | 3/2004 | Edwards et al. |
| 6,712,815 B2 | 3/2004 | Sampson et al. |
| 6,740,082 B2 | 5/2004 | Shadduck |
| 6,749,607 B2 | 6/2004 | Edwards et al. |
| 6,752,806 B2 | 6/2004 | Durgin et al. |
| 6,800,083 B2 | 10/2004 | Hiblar et al. |
| 6,837,886 B2 | 1/2005 | Collins et al. |
| 6,846,312 B2 | 1/2005 | Edwards et al. |
| 6,855,143 B2 | 2/2005 | Davison |
| 6,860,878 B2 | 3/2005 | Brock |
| 6,866,663 B2 | 3/2005 | Edwards et al. |
| 6,872,206 B2 | 3/2005 | Edwards et al. |
| 6,899,729 B1 * | 5/2005 | Cox et al. .................... 623/1.13 |
| 6,917,834 B2 | 7/2005 | Koblish et al. |
| 6,918,906 B2 | 7/2005 | Long |
| 6,923,808 B2 | 8/2005 | Taimisto |
| 6,929,642 B2 | 8/2005 | Xiao et al. |
| 6,953,469 B2 | 10/2005 | Ryan |
| 6,964,661 B2 | 11/2005 | Rioux et al. |
| 6,971,395 B2 | 12/2005 | Edwards et al. |
| 6,974,456 B2 | 12/2005 | Edwards et al. |
| 6,994,704 B2 | 2/2006 | Qin et al. |
| 7,004,938 B2 | 2/2006 | Ormsby et al. |
| 7,048,734 B1 | 5/2006 | Fleischman et al. |
| 7,056,320 B2 | 6/2006 | Utley et al. |
| 7,083,620 B2 | 8/2006 | Jahns et al. |
| 7,089,063 B2 * | 8/2006 | Lesh et al. .................... 607/101 |
| 7,122,031 B2 | 10/2006 | Edwards et al. |
| 7,125,407 B2 | 10/2006 | Edwards et al. |
| 7,150,745 B2 | 12/2006 | Stern et al. |
| 7,160,294 B2 | 1/2007 | Croft |
| 7,165,551 B2 | 1/2007 | Edwards |
| 7,167,758 B2 | 1/2007 | Baker et al. |
| 7,179,257 B2 | 2/2007 | West et al. |
| 7,293,563 B2 | 11/2007 | Utley et al. |
| 7,311,719 B2 * | 12/2007 | Bonutti ........................ 606/192 |
| 7,326,207 B2 | 2/2008 | Edwards |
| 7,329,254 B2 | 2/2008 | West et al. |
| 7,410,486 B2 * | 8/2008 | Fuimaono et al. ............. 606/41 |
| 7,416,549 B2 | 8/2008 | Young et al. |
| 7,425,212 B1 | 9/2008 | Danek et al. |
| 7,530,979 B2 | 5/2009 | Ganz et al. |
| 7,591,814 B2 * | 9/2009 | Santoianni et al. ........... 606/23 |
| 7,680,543 B2 | 3/2010 | Azure |
| 7,850,685 B2 | 12/2010 | Kunis et al. |
| 8,192,426 B2 * | 6/2012 | Stern et al. .................... 606/41 |
| 8,251,992 B2 | 8/2012 | Utley et al. |
| 8,728,073 B2 | 5/2014 | McDaniel |
| 2001/0003314 A1 * | 5/2001 | Davison et al. ............... 606/41 |
| 2001/0041887 A1 | 11/2001 | Crowley |
| 2001/0051802 A1 | 12/2001 | Woloszko et al. |
| 2002/0087151 A1 | 7/2002 | Mody et al. |
| 2002/0095160 A1 | 7/2002 | Bonutti |
| 2002/0177847 A1 | 11/2002 | Long |
| 2002/0183739 A1 | 12/2002 | Long |
| 2003/0069572 A1 | 4/2003 | Wellman et al. |
| 2003/0093117 A1 | 5/2003 | Saadat |
| 2003/0109837 A1 | 6/2003 | McBride-Sakal |
| 2003/0153905 A1 | 8/2003 | Edwards et al. |
| 2003/0181900 A1 | 9/2003 | Long |
| 2003/0181905 A1 | 9/2003 | Long |
| 2003/0191512 A1 | 10/2003 | Laufer et al. |
| 2003/0216727 A1 | 11/2003 | Long |
| 2004/0073204 A1 * | 4/2004 | Ryan et al. .................... 606/27 |
| 2004/0087936 A1 | 5/2004 | Stern et al. |
| 2004/0122452 A1 | 6/2004 | Deem et al. |
| 2004/0147916 A1 | 7/2004 | Baker |
| 2004/0153120 A1 | 8/2004 | Seifert et al. |
| 2004/0172016 A1 | 9/2004 | Bek et al. |
| 2004/0204708 A1 | 10/2004 | Edwards et al. |
| 2004/0215180 A1 | 10/2004 | Starkebaum et al. |
| 2004/0215235 A1 | 10/2004 | Jackson et al. |
| 2004/0215296 A1 | 10/2004 | Ganz et al. |
| 2004/0236316 A1 | 11/2004 | Danitz et al. |
| 2004/0243124 A1 | 12/2004 | Im et al. |
| 2005/0010095 A1 * | 1/2005 | Stewart et al. ................ 600/374 |
| 2005/0010162 A1 | 1/2005 | Utley et al. |
| 2005/0033271 A1 | 2/2005 | Qin et al. |
| 2005/0070978 A1 | 3/2005 | Bek et al. |
| 2005/0090817 A1 | 4/2005 | Phan |
| 2005/0096713 A1 | 5/2005 | Starkebaum et al. |
| 2005/0107829 A1 | 5/2005 | Edwards et al. |
| 2005/0143727 A1 | 6/2005 | Koblish et al. |
| 2005/0149013 A1 | 7/2005 | Lee |
| 2005/0154386 A1 | 7/2005 | West et al. |
| 2005/0159743 A1 | 7/2005 | Edwards et al. |
| 2005/0171527 A1 * | 8/2005 | Bhola ............................ 606/41 |
| 2005/0187546 A1 | 8/2005 | Bek et al. |
| 2005/0215983 A1 | 9/2005 | Brock |
| 2005/0245926 A1 | 11/2005 | Edwards et al. |
| 2005/0288664 A1 | 12/2005 | Ford et al. |
| 2006/0009758 A1 | 1/2006 | Edwards et al. |
| 2006/0015162 A1 | 1/2006 | Edward et al. |
| 2006/0041256 A1 | 2/2006 | Edwards et al. |
| 2006/0052773 A1 | 3/2006 | Vanney et al. |
| 2006/0069303 A1 | 3/2006 | Couvillon |
| 2006/0086363 A1 | 4/2006 | Qin et al. |
| 2006/0095032 A1 | 5/2006 | Jackson et al. |
| 2006/0100495 A1 * | 5/2006 | Santoianni et al. ........... 600/374 |
| 2006/0100619 A1 * | 5/2006 | McClurken et al. .......... 606/45 |
| 2006/0111707 A1 * | 5/2006 | O'Sullivan et al. ........... 606/41 |
| 2006/0217698 A1 * | 9/2006 | Starkebaum et al. ......... 606/32 |
| 2006/0247614 A1 | 11/2006 | Sampson et al. |
| 2006/0259028 A1 | 11/2006 | Utley et al. |
| 2006/0259029 A1 | 11/2006 | Utley et al. |
| 2006/0259030 A1 | 11/2006 | Utley et al. |
| 2006/0271032 A1 * | 11/2006 | Chin et al. .................... 606/41 |
| 2006/0282071 A1 | 12/2006 | Utley et al. |
| 2007/0010845 A1 * | 1/2007 | Gong et al. .................. 606/192 |
| 2007/0066973 A1 | 3/2007 | Stern et al. |
| 2007/0100333 A1 | 5/2007 | Jackson et al. |
| 2007/0118104 A1 | 5/2007 | Wallace et al. |
| 2007/0118106 A1 | 5/2007 | Utley et al. |
| 2007/0118159 A1 | 5/2007 | Deem et al. |
| 2007/0123922 A1 * | 5/2007 | Cooper et al. ................ 606/191 |

(56) References Cited

U.S. PATENT DOCUMENTS

| | | | |
|---|---|---|---|
| 2007/0135809 A1 | 6/2007 | Utley et al. | |
| 2007/0142831 A1 | 6/2007 | Shadduck | |
| 2007/0167963 A1 | 7/2007 | Deem et al. | |
| 2007/0219570 A1 | 9/2007 | Deem et al. | |
| 2007/0255296 A1 | 11/2007 | Sauer | |
| 2007/0287994 A1 | 12/2007 | Patel | |
| 2007/0288001 A1 | 12/2007 | Patel | |
| 2008/0086073 A1* | 4/2008 | McDaniel | 604/22 |
| 2008/0097427 A1* | 4/2008 | Stern et al. | 606/41 |
| 2008/0177228 A1* | 7/2008 | Burton | 604/103.06 |
| 2008/0275445 A1 | 11/2008 | Kelly et al. | |
| 2008/0319348 A1* | 12/2008 | Nakajima et al. | 600/585 |
| 2008/0319350 A1 | 12/2008 | Wallace et al. | |
| 2009/0012512 A1* | 1/2009 | Utley | A61B 18/1492 606/21 |
| 2009/0012513 A1 | 1/2009 | Utley et al. | |
| 2009/0012518 A1 | 1/2009 | Utley et al. | |
| 2009/0036733 A1 | 2/2009 | Wallace et al. | |
| 2009/0043301 A1* | 2/2009 | Jarrard et al. | 606/41 |
| 2009/0048593 A1 | 2/2009 | Ganz et al. | |
| 2009/0336886 | 2/2009 | Utley et al. | |
| 2009/0177194 A1 | 7/2009 | Wallace et al. | |
| 2009/0187181 A1 | 7/2009 | Shadduck | |
| 2009/0275934 A1* | 11/2009 | Baxter et al. | 606/15 |
| 2009/0299355 A1* | 12/2009 | Bencini et al. | 606/21 |
| 2009/0318914 A1 | 12/2009 | Utley | |
| 2010/0063495 A1 | 3/2010 | Utley et al. | |
| 2010/0191237 A1 | 7/2010 | Shadduck | |
| 2010/0204560 A1* | 8/2010 | Salahieh et al. | 600/373 |
| 2010/0234840 A1 | 9/2010 | Jackson et al. | |
| 2012/0059368 A1 | 3/2012 | Takaoka et al. | |
| 2012/0239028 A1* | 9/2012 | Wallace et al. | 606/41 |

FOREIGN PATENT DOCUMENTS

| | | |
|---|---|---|
| DE | 3838840 | 5/1990 |
| DE | 4303882 | 8/1994 |
| EP | 0105677 A1 | 4/1984 |
| EP | 0115420 A2 | 8/1984 |
| EP | 0139607 B1 | 5/1985 |
| EP | 0251745 A1 | 1/1988 |
| EP | 0521595 A2 | 1/1993 |
| EP | 0608609 B1 | 8/1994 |
| EP | 1323382 A1 | 7/2003 |
| EP | 1634542 B1 | 3/2006 |
| EP | 2415495 A1 | 8/2012 |
| JP | 8-506738 | 7/1996 |
| JP | 2001120565 | 5/2001 |
| JP | 2001523987 | 11/2001 |
| JP | 2005503181 | 2/2005 |
| JP | 2009-509713 | 3/2009 |
| JP | 2009517130 | 4/2009 |
| JP | 2009520572 | 5/2009 |
| JP | 2010532702 | 10/2010 |
| JP | 2010532702 A | 10/2010 |
| JP | 2011-218189 | 11/2011 |
| WO | WO 91/01773 A1 | 2/1991 |
| WO | WO 91/03207 A1 | 3/1991 |
| WO | WO 92/10142 A1 | 6/1992 |
| WO | WO 93/08755 A1 | 5/1993 |
| WO | WO 94/07446 A1 | 4/1994 |
| WO | WO 94/10925 A1 | 5/1994 |
| WO | WO 94/21165 A1 | 9/1994 |
| WO | WO 94/22366 A1 | 10/1994 |
| WO | WO 94/26178 A1 | 11/1994 |
| WO | WO 95/18575 A1 | 7/1995 |
| WO | WO 95/19142 A1 | 7/1995 |
| WO | WO 95/25472 A1 | 9/1995 |
| WO | WO 96/00042 A1 | 1/1996 |
| WO | WO 96/16606 A1 | 6/1996 |
| WO | WO 96/29946 A1 | 10/1996 |
| WO | WO 97/04702 A1 | 2/1997 |
| WO | WO 97/06857 A2 | 2/1997 |
| WO | WO 97/32532 A1 | 9/1997 |
| WO | WO 97/43971 A1 | 11/1997 |
| WO | WO 98/12999 A2 | 4/1998 |
| WO | WO 98/14238 A1 | 4/1998 |
| WO | 9819613 | 5/1998 |
| WO | WO 98/18393 A1 | 5/1998 |
| WO | WO 99/03413 A1 | 1/1999 |
| WO | WO 99/35987 A1 | 7/1999 |
| WO | WO 99/42046 A1 | 8/1999 |
| WO | WO 99/55245 A1 | 11/1999 |
| WO | WO 00/01313 A1 | 1/2000 |
| WO | WO 00/59393 A1 | 10/2000 |
| WO | WO 00/62699 A2 | 10/2000 |
| WO | WO 00/66021 A1 | 11/2000 |
| WO | WO 00/66617 A1 | 11/2000 |
| WO | WO 00/69376 A1 | 11/2000 |
| WO | WO 01/22897 A1 | 4/2001 |
| WO | WO 01/35846 A1 | 5/2001 |
| WO | WO 01/45550 A2 | 6/2001 |
| WO | WO 01/89440 A2 | 11/2001 |
| WO | WO 02/096327 A2 | 12/2002 |
| WO | WO 03/070091 A1 | 8/2003 |
| WO | 2005070316 A1 | 8/2005 |
| WO | WO 2007/001981 A2 | 1/2007 |
| WO | 2007044244 A2 | 4/2007 |
| WO | 2007061984 A2 | 5/2007 |
| WO | WO2012/174375 A1 | 12/2012 |
| WO | 2013028425 A1 | 2/2013 |

OTHER PUBLICATIONS

Dallamagne et al; Laparoscopic Nissen Fundoplication: Preliminary. Surgical Laparoscopy and Endoscopy. 1991; 1(3):138-143.

Hinder et al; The Technique of Laparoscopic Nissen Fundoplication. Surgical Laparoscopy and Endoscopy. 1992; 2(3):265-272.

Kaneko et al; Physiological Laryngeal Pacemaker. Trans Am Soc. Artif Intern Organs. 1985; XXXI:293-296.

Karlstrom et al; Ectopic Jejunal Pacemakers and Enterogastric Reflux Roux Gastrectomy: Effect of Intestinal Pacing. Surgery. 1989; 106(3):486-495.

Kelly, K.A. et al; Duodenal-Gastric Reflux and Slowed Gastric Emptying by Electrical Pacing of the Canine Duodenal Pacesetter Potential. Gastroenterology. 1977; 72(3):429-433.

Mugica, et al. Direct Diaphragm Stimulation. PACE. 1987; 10:252-256.

Mugica, et al., Preliminary Test of a Muscular Diaphragm Pacing System on Human Patients. Neurostimulation: An Overview, chapter 21. 1985; 263-279.

Reynolds, J.C. Influence of Pathophysiology, Severity, and Cost on the Medical Management of Gastroesophageal Reflux Disease. Am J. Health-Syst Phar. 1996; 53(22sul3):S5-S12.

Rice et al; Endoscopic Paranasal Sinus Surgery. Chapter 5, Functional Endoscopic Paranasal Sinus Surgery, The Technique of Messerklinger. Raven Press. 1988; 75-102.

Rice et al; Endoscopic Paranasal Sinus Surgery. Chapter 6, Total Endoscopic Sphenoethmoidectomy. The Technique of Wigand. Raven Press. 1988; 103-125.

Rodriguez et al.(ASGE Technology Committee); Technology Status Evaluation Report,; Mucosal ablation devices; Gastoinestinal Endoscopy; vol. 68; No. 6; pp. 1031-1042; Dec. 2008.

Salameh et al; An Animal Model Study to Clarify and Investigate Endoscopic Tissue Coagulation by Using a New Monopolar Device. Gastrointestinal Endoscopy; 2004; 59 (1): 107-112.

Urshel, J.D. Complications of Antireflux Surgery. Am J. Surg. 1993; 166 (1):68-70.

Jackson, Jerome; U.S. Appl. No. 13/181,484 entitled "Methods and systems for treatment of tissue in a body lumen," filed Jul. 12, 2011.

Utley et al.; U.S. Appl. No. 13/181,490 entitled "Precision ablating method," filed Jul. 12, 2011.

Jackson et al.; U.S. Appl. No. 13/189,793 entitled "Methods and Systems for Determining Physiologic Characteristics for Treatment of the Esophagus," filed Jul. 25, 2011.

Notification of the First Office Action from the State Intellectual Property Office of the People's Republic of China dated Jul. 8, 2015 for Application No. 201280021105.4.

(56) References Cited

OTHER PUBLICATIONS

Office Action for Patent Application JP 2014-217121 dated Sep. 9, 2015 from Japanese Patent Office with Translation.
Patent Examination Report No. 2 for Patent App. No. 2012231245, dated Mar. 7, 2016, from the Australian Government IP Australia.
Official Action for Application No. 2013146545, from the Federal Service for Intellectual Property (FIIP), Moscow, Russia dated Mar. 22, 2016.
Notification of the Second Office Action for Chinese Application No. 201280021105.4, dated Jan. 5, 2016, from the State Intellectual Property Office of the People's Republic of China.
Patent Examination Report No. 1 for Australian Application No. 2012231245 from the Australian Government IP Australia dated Oct. 27, 2015.
Third Office Action issued by the Chinese Patent Office for Chinese Application No. 201280021105.4 dated Jul. 12, 2016.
European Examination report for Application No. 12713452.6 from the European Patent Office dated Jul. 10, 2017.
Notice of Reasons for Rejection for Japanese Patent App. No. 2016-0139994 dated May 23, 2017 from the Japanese Patent Office.

\* cited by examiner

SELECTIVELY EXPANDABLE OPERATIVE ELEMENT SUPPORT STRUCTURE AND METHODS OF USE

INCORPORATION BY REFERENCE

All publications, patents, and patent applications mentioned in this specification are herein incorporated in their entirety by reference for all purposes to the same extent as if each individual was specifically and individually indicated to be incorporated by reference.

FIELD OF THE INVENTION

This application is related to the devices and techniques of providing therapy to tissue. More particularly, the invention relates to ablating target tissue in the gastrointestinal tract with radiofrequency energy.

BACKGROUND OF THE INVENTION

The present invention relates devices and techniques for providing therapy to tissue. Currently, the ability to properly position an instrument to provide treatment to a tissue site may be hindered by the location of that treatment site within the body. Additional challenges may arise by the anatomical variation or makeup of the tissue site. As a result, there is a need for diagnostic or therapeutic instruments adapted to provide therapy or diagnosis to tissue sites within the body.

SUMMARY OF THE INVENTION

In one embodiment of the present invention, there is provided a device having an expandable support member having a first portion and a second portion. The first portion is adapted to have a smaller expansion index than the second portion. An operative element is supported at least in part by the expandable support member. The operative element may be a therapeutic or diagnostic instrument. In various embodiments, the operative element is supported in whole or in part by the first portion. In various embodiments, the operative element is supported in part by the second portion. In one aspect, the surface area of the expandable support member first portion is substantially the same as the surface area of the diagnostic or therapeutic instrument, referred to in various respects as operative element. In various embodiments, the surface area of the expandable support member first portion is essentially equal to the surface area of the operative element. In various embodiments, the surface area of the expandable support member first portion is less than the surface area of the operative element. In various embodiments, the surface area of the expandable support member first portion is greater than the surface area of the therapeutic instrument.

In various embodiments, the expansion index of the expandable support member first portion is substantially 1. In various embodiments, the expansion index of the expandable support member first portion is greater than 1. In various embodiments, the expansion index of the expandable support member first portion is less than 1.

In various embodiments, the expansion index of the expandable support member second portion is greater than the first portion. In various embodiments, the expansion index of the expandable support member second portion is about 1. In various embodiments, the expansion index of the expandable support member second portion is greater than 1. In various embodiments, the expansion index of the expandable support member second portion is between about 1 and about 10, preferably between about 5 and about 10. In various embodiments, the expansion index of the expandable support member second portion is between about 1 and about 5. In various embodiments, the expansion index of the expandable support member second portion is greater than 1 and less than 10. In various embodiments, the expansion index of the expandable support member second portion is about 1.2. In various embodiments, the expansion index of the expandable support member second portion is about 1.4. In various embodiments, the expansion index of the expandable support member second portion is about 1.8.

In various embodiments, the first portion and the second portion of the expandable support member are distinct elements. In various embodiments, the first portion and the second portion of the expandable support member are contiguous. In various embodiments, the first portion and the second portion of the expandable support member are integrally formed. In various embodiments, the first portion and the second portion of the expandable support member are positioned adjacent one another. In various embodiments, the expandable support member comprises a third portion having a different expansion index than the first portion and the second portion. The third portion may be distinct from the first portion and the second portion. The third portion may be integrally formed with one or either of the first portion and second portion.

In another aspect, the expansion index of the expandable support member second portion includes circumferential expansion. Additionally, the expansion index of expandable support member second portion may include expansion generally orthogonal to the circumferential expansion. In still another aspect, when the expandable support member is expanded the surface area of the therapeutic or diagnostic element may be different than the surface area of the expandable element second portion. In another aspect, the wall thickness of the expandable support member first portion is greater than the wall thickness of the expandable support member second portion. In another aspect, the wall thickness of the expandable support member second portion has variable wall thickness. In various embodiments, the first portion and second portion comprise different materials, the second portion being formed of a material selected to have a higher expansion index than the first portion. In various embodiments, one of the first portion, second portion, and a combination of the same is formed of material or materials selected to have a predetermined expansion index. In various embodiments, the expandable support member second portion is formed of a relatively rigid material.

In various embodiments, a portion of the expandable support member corresponding to the second portion is curvilinear and substantially cylindrical. In various embodiments, when the expandable support member is in an expanded state, the cross section of the second portion is curvilinear and has a second radius. In various embodiments, in the expanded state, cross section of the first portion is curvilinear and has a first radius, the first radius being smaller than the second radius. In various embodiments, the expandable support member is substantially tubular. In various embodiments, the expandable support member comprises a balloon. The expandable support member may have a non-tubular shape. In various embodiments, the expandable support member is furled around an expansion member and adapted to expand by unfurling.

In still another aspect, the therapeutic or diagnostic instrument is an electrode array. In another aspect, the therapeutic or diagnostic instrument can transmit energy to ablate tissue.

In another aspect, there is also provided one or more reinforcing elements on or within the expandable support structure first portion. In one additional aspect, the reinforcing elements are an electrode array assembly. In still an additional aspect, the reinforcing elements are part of the therapeutic or diagnostic device.

In another embodiment of the present invention, there is provided a device including an expandable support member having a first portion and a second portion. The support member is adapted for non-uniform expansion of the first and second portions. There is also a therapeutic or diagnostic instrument supported at least in part by the expandable support member first portion. In one aspect, the support member first portion has about the same surface area as the therapeutic or diagnostic instrument. In another aspect, most of the expansion occurs in the second portion when the expandable support member expands. In another aspect, there is also provided an area of substantially limited expansion within the expandable support member first portion. In still another aspect, the area of substantially limited expansion comprises a reinforcing element.

In another embodiment of the present invention, there is a method of providing therapy to tissue in a body. The method includes the step of positioning an instrument in proximity to tissue in a body selected to receive therapy. The instrument is being supported by an expandable support member adapted for non-uniform expansion between a first portion and a second portion. The first portion supports at least part of the instrument. Next, the method includes the step of expanding the expandable support member second portion until the instrument is a therapeutic position relative to the tissue in a body selected to receive therapy. The method also includes the step providing therapy to tissue selected to receive therapy using the instrument. The method also includes the step of diagnosing at the treatment site using the instrument. In one aspect, the therapeutic position is where the instrument is in contact with the tissue selected to receive therapy. In another aspect, the therapeutic position is where the instrument is spaced apart from the tissue selected to receive therapy. In an additional aspect, the providing therapy step includes providing therapy to tissue selected to receive therapy using the instrument by ablating some of the tissue selected to receive therapy. In another aspect, the providing therapy step includes providing therapy to tissue selected to receive therapy using the instrument by obtaining information about some of the tissue selected to receive therapy.

The devices and methods of the invention have other features and advantages which will be apparent from or are set forth in more detail in the accompanying drawings, which are incorporated in and form a part of this specification, and the following Detailed Description of the Invention, which together serve to explain the principles of the present invention.

DETAILED DESCRIPTION OF THE INVENTION

Figure 1:
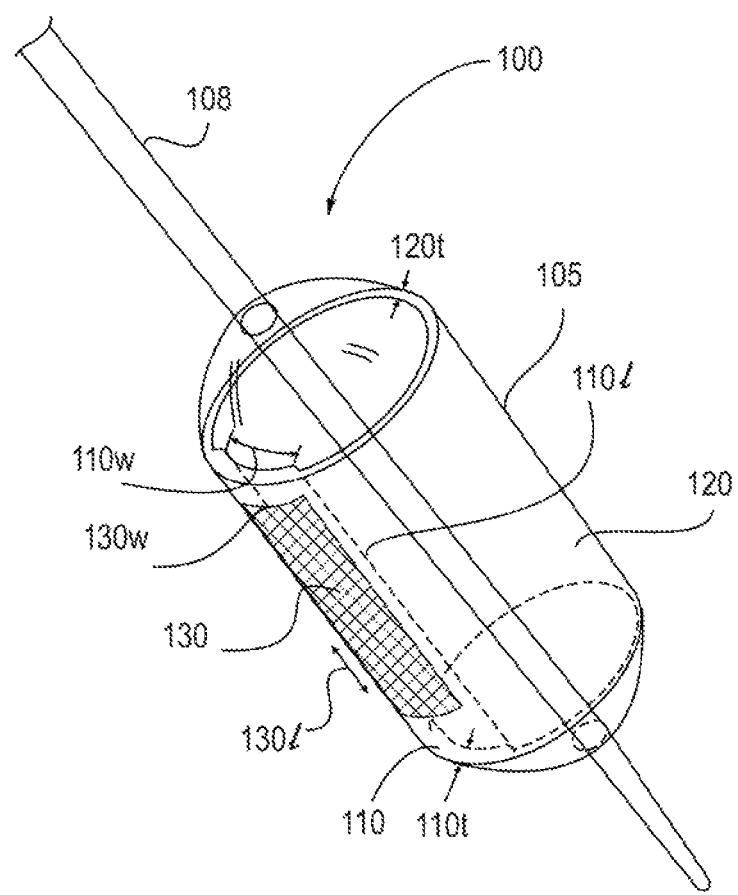
FIG. 1 is a perspective view of an embodiment of a device including an expandable support member.

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

For convenience in explanation and accurate definition in the appended claims, the terms "up" or "upper", "down" or "lower", "inside" and "outside" are used to describe features of the present invention with reference to the positions of such features as displayed in the figures.

In many respects the modifications of the various figures resemble those of preceding modifications and the same reference numerals followed by subscripts "a", "b", "c", and "d" designate corresponding parts.

The invention relates to devices that provide therapy directed to the inner aspect of walls of hollow or luminal organs as typically exemplified by organs of the gastrointestinal tract. These devices generally include an operative element. In various embodiments, the operative element is a therapeutic or diagnostic instrument for delivering to a treatment site. Some of these devices have an operative element that comes into direct contact with a target. The operative element may be brought into effective contact with a target, at least in part, by way of a volumetric expansion of a member or support structure that causes pressing of an operative element against the target site. Generally accompanying volumetric expansion of an expandable member is surface area expansion of its surrounding curviplanar surface. If an operative element, such as an ablation element, is mounted directly on a support structure whose volume expands, the expansion of the surface area that supports the operative element can potentially complicate the consistency of energy delivery from an ablation structure. For example, an ablation structure may be configured such that it delivers ablational energy from radiofrequency elements distributed at a particular energy density per unit surface area. When the surface area of the support varies, the density of energy delivery from an ablational structure integrated onto, or intimately connected to such varying surface area may vary. A varying density of energy delivery elements can complicate control mechanisms or processes that rely on, or are subject to better control, if such energy delivery element density is held constant. The devices and methods described and depicted herein provide a solution to this problem by sectoring an instrument support surface that is expandable as a whole into at least two portions, a first portion which supports the ablational instrument and which expands to a minimal degree, and another portion or portions with which the instrument is not associated, and which provides the entirety or substantial majority of the expandability of the support.

In some embodiments of the invention, the expandable member, itself, is sectored into partially circumferential regions of differing distensibility, such differences arising from differences in thickness of the expandable member sheet, by differences in the composition of the expandable member in two or more portions or sectors, or by inclusion or integration of elements within the surface that constrain the distensibility of sectors of the expandable member. In these embodiments, an operative element is typically arranged on a sector of the expandable member that is substantially non-expanding across its surface, the expandability of the member being contributed by another, or a second portion of the member. In other embodiments, the member itself is not necessarily sectored into portions that differ in inherent distensibility, but rather, a non-distensible, or substantially non-distensible material is adhered or coupled to a partially-circumferential portion of the surface of the expandable member. Such dimensionally-stabilizing material or feature may be associated with either the interior or the exterior surface of the expandable member. In some embodiments, a material adhered to the exterior surface of the expandable member is used directly as a support for an operative element such as an electrode array.

Thus, non-expandability of a region of an expandable member that supports an operative element may be attributed substantially to (1) non-expandability of a portion of the surface of the member, or to (2) a constraint on expandability of a portion of a surface by a non-expansive material adhered or coupled to a portion of the surface of a member that is otherwise as expandable as other regions of the member surface. In a third type of embodiment, multiple expansion-constraining features may contribute to the non-expandability of a region of an expandable member surface. For example, limitations on expandability may be contributed by difference in thickness of composition of a region, and/or by integration of expansion-limiting elements directly into the expandable member surface, and/or by adhesion or coupling of a non-distensible material to either the interior or exterior surface of the expandable member. This non-expandable portion is referred to in various respects to as a non-distendible portion.

From the perspective of the operative element, it is indifferent to the approach or combination of approaches that dimensionally stabilize the surface upon which it rests, what advantageously serves it is simply the dimensional stability of its substrate. There may be particular advantage to the device as a whole, however, as provided by limitations on expandability of the surface that are associated with the thickness or composition of the expandable member even with the presence of a non-distensible support for the operative element. A non-distensibility that is provided solely by adhesion of a non-distensible backing on an otherwise distensible surface may create stress between the surface of the member and the non-distensible backing. Such stress may be distributed across the zone of adhesion, however it may also be particularly focused at the portion of the expandable member surface that defines the edge between the feely expandable region and the portion that is expandably-constrained by the adhered material. Embodiments of the invention are generally described as providing an operative element such as a diagnostic of therapeutic element. Further, examples are described in the context as providing ablational energy, as for example delivered by radiofrequency energy, which ablates by ohmic heating. The invention however, is not limited by these particular examples. Diagnostic elements, for example, such as biopsy probes may be delivered by instruments that make use of embodiments of the expandable support member provided. Further, in terms of ablational instruments that can be carried and therapeutically positioned by embodiments of the expandable member, elements that deliver forms of energy other than radiofrequency, such as microwave, ultrasonic, resistive heating, chemical, cryogenic, a heatable fluid, and optical including without limitation, ultraviolet, visible, infrared, collimated or non collimated, coherent or incoherent, or other light energy, are all included as embodiments of the invention. It will be further appreciated that some forms of energy, such as optical energy, can be used in combination with one or more sensitizing agents. One will appreciate from the description herein that other types of operative elements may be used in accordance with the invention. The operative element may include a diagnostic instrument. Examples of suitable diagnostic instruments include, but are not limited to, a biopsy array or other testing fixture or instrument to test or determine one or more qualities or characteristics of the tissue. The device may also include a visualization structure for visualizing the target region during positioning and treatment. Other examples of operative elements, instruments, and constituent components for use with the device in accordance with the invention are described in greater detail in U.S. Pat. Nos. 6,551,310, 7,530,979, 7,150,145, 7,344,535, 6,872,206, 7,507,234, U.S. application Ser. No. 11/633,938, now U.S. Patent Pub. No. 2007/0100333, and U.S. application Ser. No. 11/286,257, now U.S. Patent Pub. No. 2007/0135809, the entire contents of which patents and publications are incorporated herein for all purposes by this reference.

Typical embodiments of radiofrequency elements that may be carried on the surface of some of the embodiments of the exemplary expandable members described below are bipolar electrode arrays. One will appreciate, however, that the devices in accordance with the invention may utilize other electrode structures including, but not limited to, monopolar electrodes in conjunction with an indifferent electrode. U.S. Pat. No. 7,150,745 to Stern (issued Dec. 19, 2006), which is hereby incorporated into this application, provides examples of electrode arrays (FIGS. 6A-7D) that may be advantageously utilized in combination with embodiments of the expandable member provided herein. As will be described below, other energy delivery elements are envisioned within the scope of the invention.

In general, the purpose of expanding an expandable support is to bring an operative element such as an ablation structure into therapeutically effective contact with a tissue site targeted for ablation. With such contact, various non-penetrating electrode patterns may be employed to deliver ablational energy to a targeted contiguous radial site of the gastrointestinal tract. Various aspects of the invention relate to electrode patterns and methods for controlling the delivery of radiofrequency energy into tissue in three dimensions: controlling energy delivery across the surface area of tissue within the target area, and controlling delivery into the depth of tissue within the target area such that some volume portion of the tissue is ablated and some volume portion of the tissue is not ablated. Examples of electrode patterns suitable for use with the device in accordance with the invention are provided in U.S. application Ser. No. 12/114,628 to Kelly et al., as filed on May 2, 2008, which is incorporated herein for all purposes by this reference. Embodiments of this type of ablation may be understood as a fractional ablation or a partial ablation within a contiguous target or treatment area, as such, the post-ablationally-treated area of tissue has a mixed pattern of affected tissue and areas of substantially unaffected tissue.

A better understanding of the features and advantages of the present invention will be obtained by reference to the following detailed description of exemplary embodiments as shown in FIGS. 1-14C, in which the principles of the invention are utilized in exemplary embodiments.

FIG. 1 is a perspective view of an embodiment of a diagnostic or therapeutic device 100 including an expanded expandable support member 105 and an operative element 130 arranged on the expandable support member. The expandable support member 105 has a generally cylindrical configuration with rounded or hemispherical ends, and is mounted on a shaft 108. In some embodiments, as shown in FIG. 1, the shaft, or a portion or an extension thereof proceeds through the expandable member and emerges distally to form a distally leading structure that stabilized the structure of the expandable member and provides operational advantages during deployment of the device. The expandable support member 105 includes a first portion 110 and a second portion 120. An operative element 130, such as a therapeutic or diagnostic instrument or structure, is supported by the expandable support member first portion 110. An exemplary therapeutic instrument 130 may be an ablational structure, configured to deliver radiofrequency energy to a target tissue in the body, and an exemplary shaft 108 may be a catheter suitably sized and configured to enter and be advanced into the gastrointestinal tract. Various conventional components such as a generator and control system, wiring, electrical connections and user interface may be used to operate the operative element 130 and possibly elements of shaft 108. These conventional component details are omitted from the figures for clarity and to allow a focus on the invention.

FIG. 1 also shows some particular structural details of the expandable support member 105. The operative element 130, as may be exemplified by an ablational structure, has a surface area defined by a length 130*l* and a width 130*w*. It may be appreciated that embodiments of the expandable support member are generally cylindrical, with their longitudinal axis parallel to the longitudinal axis of the shaft or elongate member upon which they are supported. In contrast, the operative element 130 arranged on the expandable support member typically occupies an arc of less than 360 degrees around the expandable member, and consequently, an arc of less than 360 degrees around shaft. In general, in the method of use of the device, the expandable support member is expanded to fill the interior of a body lumen or hollow organ being treated. Thus, the fraction of a circumference that the operative element occupies on the expandable member corresponds to the fraction of a circumference of the hollow organ that is being contacted by the operative element during any single treatment delivery provided by the operative element. As such, these devices and methods are generally appropriate for focused treatment of target sites that occupy a fraction of the circumference of a hollow organ, rather than a treatment that needs to directed to a fully circumferential region. Such focal target arcs may, for example, be less than 360 degrees, about 180 degrees, between about 20 degrees and about 180 degrees, less than 180 degrees, between about 20 degrees and about 90 degrees, less than 180 degrees, about 90 degrees, or any circumferential arc smaller than 90 degrees.

As shown in FIG. 1, the expandable support member first portion 110 has a surface area defined by a length 110*l* aligned with the longitudinal axis of the support member, and a width 110*w* aligned with a radial axis of the support member. In this embodiment, the surface area of the expandable support member first portion 110 is greater than that of the operative element 130 because both the length and the width of the expandable support member first portion are greater than both the length and the width of the operative element 130. Alternatively, the expandable support member first portion may also have a larger surface area by having the same width as the instrument but greater length or by having the same length but greater width.

The embodiment shown in FIG. 1 has a wall thickness 110*t* of the expandable support first portion 110 that is greater than the wall thickness 120*t* of the expandable support second portion 120. The expandable support member wall thickness 110*t* and 120*t* are both uniform along the length and width of the portions 110, 120, respectively. Either one or both of the expandable support member portions (first portion and second portion) may also have non-uniform or variable wall thickness.

In one aspect, the expandable support member first portion 110, which supports the ablation instrument, is adapted to have a smaller expansion index than the expandable support member second portion 120. The expansion index for a given expandable support structure or portion of an expandable support structure refers to the final surface area of a selected portion of the structure (as it is being subjected to a particular expansive force) divided by the initial surface area of the selected portion of the structure.

As used herein, "expansion index" generally refers to the ratio of an expanded surface dimension relative to an unexpanded surface dimension for a given object under a specified load, all other things equal. The dimension includes, but is not limited to, a length, a surface area, and a volume. In various respects, "expansion index" is expressed numerically. If the object expands when subjected to the load, it is said to have an expansion index greater than 1. If the object does not expand when subjected to the load, it is said to have an expansion index equal to 1. If the object shrinks when subjected to the load, it is said to have an expansion index less than 1. In various embodiments, the expansion is entirely or mostly elastic, meaning, the material recovers to substantially its original shape and/or size. In various embodiments, the non-distendible portion (e.g. first portion) has a maximum expansion index of 1.2, preferably 1.1. In various embodiments, the non-distendible portion (e.g. first portion) has a maximum expansion index of about 1. In various embodiments, the expandable portion (e.g. second portion) has a maximum expansion index of 10 (i.e. 1000% expansion).

In various embodiments, the first portion of the expandable support member, when subjected to a particular expansive force, expands minimally. It either does not expand at all (expansion index of 1.0) or it expands to a small degree (and expansion index slightly greater than 1). In brief, it may be understood that an expansion index of a surface that expands minimally when subjected to a particular expansive force is about 1.

On the other hand, areas of the support structure not used to support the therapeutic instrument or element may have an expansion index that is significantly greater than one (1), or even a multiple of one (1). As explained below in the context of exemplary figures, various portions of the expandable support structure are configured to respond to expansion forces differently. And, as explained in the examples below, any of a variety of techniques or methods of manufacture may be used singularly or in combination to produce the desired expansion ratio in each of the two portions of the expandable support. In various embodiments, the expandable support member includes one or more other portions having a different expansion index than the first portion and the second portion. The one or more other portions may be contiguous with either or both of the first portion and second portion.

Figure 2A:
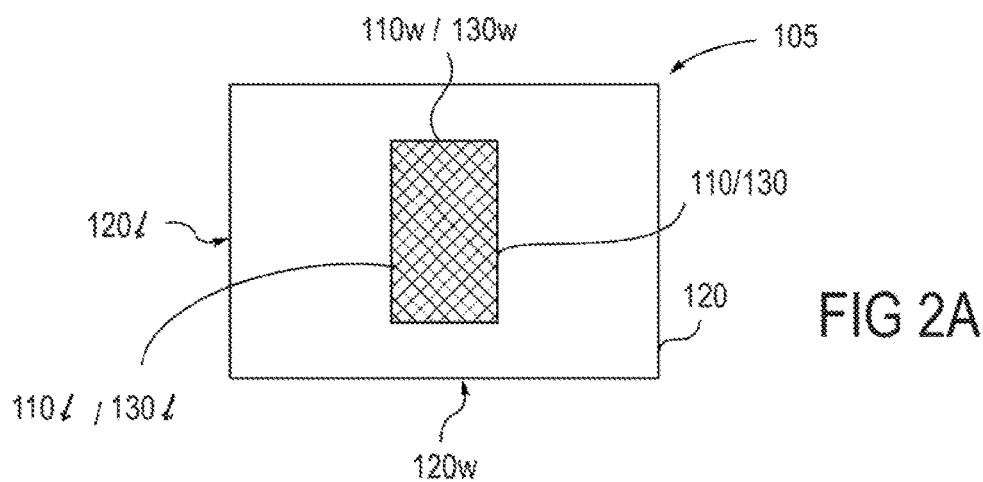
FIGS. 2A and 2B illustrate, respectively, an expandable support member in an unexpanded condition and an expanded condition where the expandable support member first portion has an expansion ratio of one (1).
Figure 2B:
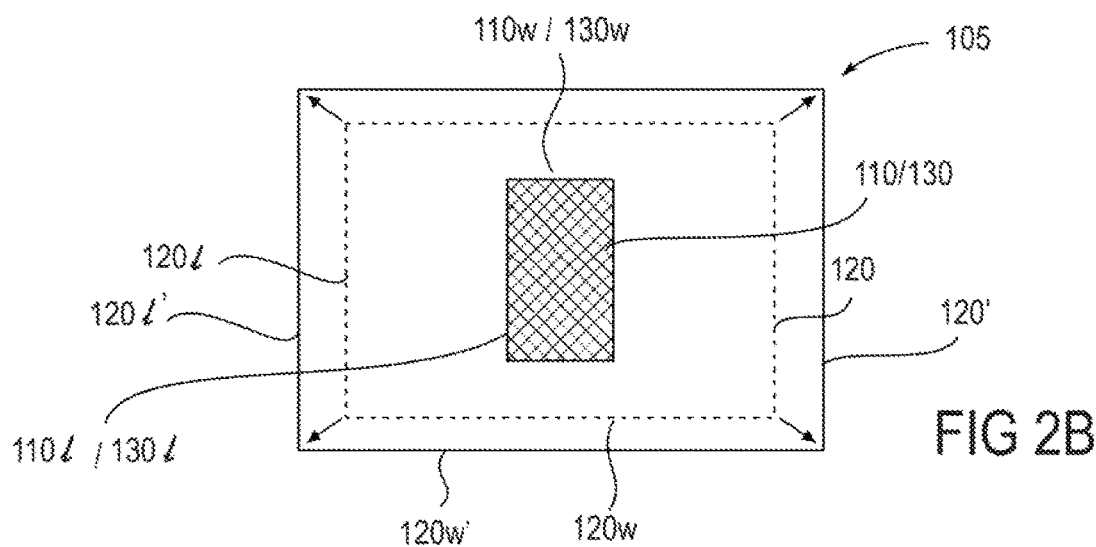

FIGS. 2A and 2B show an expandable support member 105 as a two dimensional representation of a curviplanar sheet in an unexpanded condition and an expanded condition, respectively. As seen in this illustrative embodiment, the expandable support member first portion has an expansion ratio of one (1), i.e., it does not expand when subjected to a particular force that causes the second portion to expand. FIG. 2A shows an expandable support member 105 in an initial or unexpanded condition; the expandable member first portion 110 has a width 110w and a length 110l. In this embodiment, the operative element 130 has a width 130w and a length 130l which are the same as those of the expandable support member first portion. The expandable support member second portion 120 has a width 120w and a length 120l.

FIG. 2B shows the expandable support member 105 of FIG. 2A in an expanded condition. The expandable support member achieves an expanded condition wholly because of the expansion of the expandable member second portion into an expanded condition (120') that includes expansion along two axes, i.e., in both length and width (in contrast to the absence of contribution of first portion to such expansion). In the expanded condition of FIG. 2B, the second portion width 120w has increased to width 120w' and the second portion length 120l has increased to length 120l'. As a result, the expansion ratio of the expandable support member second portion 120 is greater than one (1). In this embodiment, the area of the operative element 130 is the same as the area for the expandable support member first portion 110. The areas of expandable support member first portion 110 and the operative element 130 remain the same in both the unexpanded (FIG. 2A) and expanded (FIG. 2B) configuration. As a result, the expansion ratio of the expandable support member first portion 110 and the operative element is one (1).

Figure 3A:
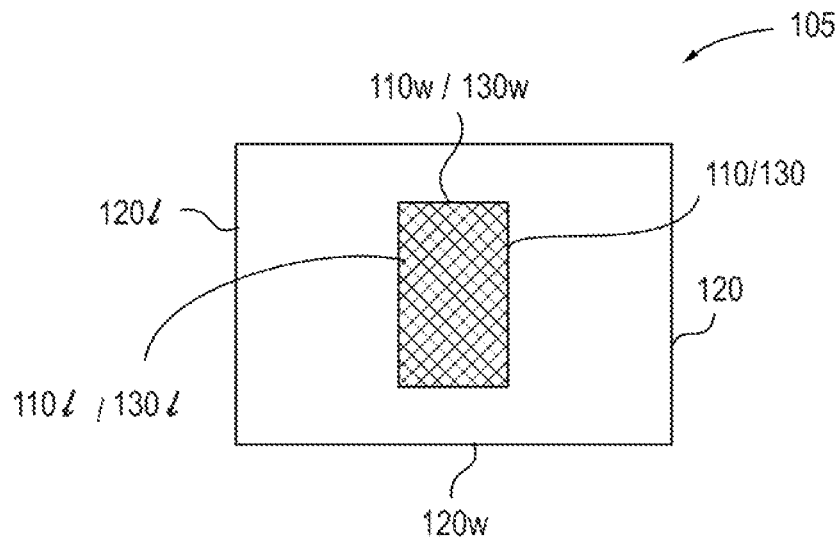
FIGS. 3A and 3B illustrate, respectively, an expandable support member in an unexpanded condition and an expanded condition where the expandable support member first portion has an expansion ratio of about 1.
Figure 3B:
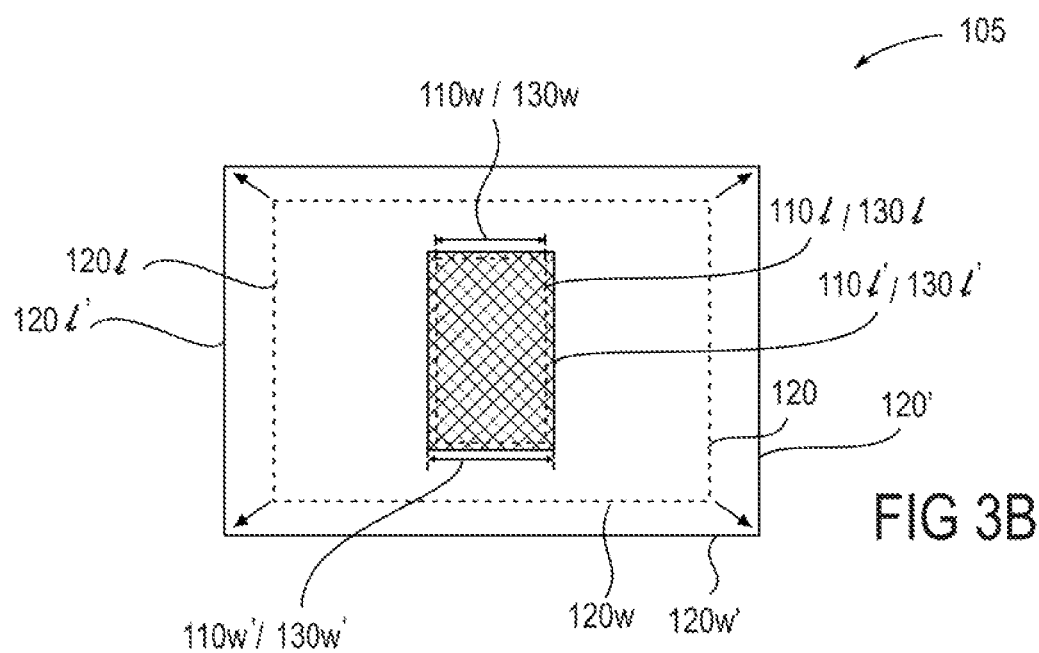

FIGS. 3A and 3B show an expandable support member 105 in an unexpanded condition and an expanded condition, respectively. In this embodiment, the expandable support member first portion has an expansion ratio of about one (1). FIG. 3A illustrates an expandable support member 105 in an initial or unexpanded condition. The expandable member first portion 110 has a width 110w and a length 110l. In this embodiment, the therapeutic or diagnostic instrument 130 has a width 130w and a length 130l. In this embodiment, the therapeutic or diagnostic instrument area is the same as the area for the expandable support member first portion. The expandable support member second portion 120 has a width 120w and a length 120l.

FIG. 3B show the expandable support member 105 of FIG. 3A in an expanded condition. The expandable support member achieves an expanded condition because of the expansion of the expandable member second portion into an expanded condition (120') along two axes, .i.e., both length and width. In the simple two dimensional expandable support member 105, shown in FIGS. 3A and 3B, most of the expansion occurs in expandable support member second portion 120 and some expansion occurs in the expandable support member first portion 110. While the expandable support member second portion 120 expands in both length and width, the expandable support member first portion 110 and the operative element 130 expands only in width. In this example, the expansion ratio of the expandable support member second portion 120 is greater than 1. In the expanded condition of FIG. 3B, the second portion width 120w has increased to width 120w' and the second portion length 120l has increased to length 120l'. Additionally, the first portion width 110w has increased to width 110w' and the first portion length 110l has increased to length 110l'. As a result, the expansion ratio of the expandable support member second portion 120 is greater than 1. The expansion of the second portion is greater than the expansion of the first portion. Note also that there is also an expansion of the operative element 130. The operative element width 130w has increased to width 130w' and the operative element length 130l has increased to length 130l'. As a result of the amount of expansion in expandable support member first portion 110 and the operative element 130, the expansion ratio of the expandable support member first portion 110 and the operative element 130 is about one (1).

FIGS. 2A, 2B, 3A and 3B are shown as two-dimensional sheet-like structures for visual simplicity in conveying the concept of an expansion index that occurs in a curviplanar structure. It is to be appreciated that the expansion of the expandable support member overall or the first and/or second expandable support members portions may expand in more complex manner or in a manner related to the structure, form, or configuration of the expandable support member, the expandable support member first portion or the expandable support member second portions.

In typical embodiments of the invention, a therapeutic or diagnostic instrument, such as an ablational structure, is supported on, or integrated into a curviplanar surface, such as the wall or surface of an expandable balloon. Setting aside, for the moment, differences in the degree to which different regions of portions of a balloon surface are distensible or expandable, expansion of the surface area may occur homogenously across a surface area, or it may occur preferentially along one or more axes within the curviplanar context. For example, expansion may occur along a first axis within the curved plane, or along a first and second axis, perpendicular to the first axis. Alternatively, the second axis may be oriented at an angle other than 90 degrees to the first axis. By way of another example, a first axis may be aligned orthogonally to the longitudinal axis of a cylindrical balloon as the circumference of the balloon expands. And a second axis may be aligned longitudinally, in parallel to the longitudinal axis of the balloon, as the surface of the balloon lengthens upon expansion. The axes along which expansion occurs may be more complex than these examples of two perpendicular axes, and may vary across the surface of an expandable member, and may be subject to influence by the composition of the member, by the integration or attachment of features to the wall of the member, or by variation in the thickness of the wall composition.

Figure 4A:
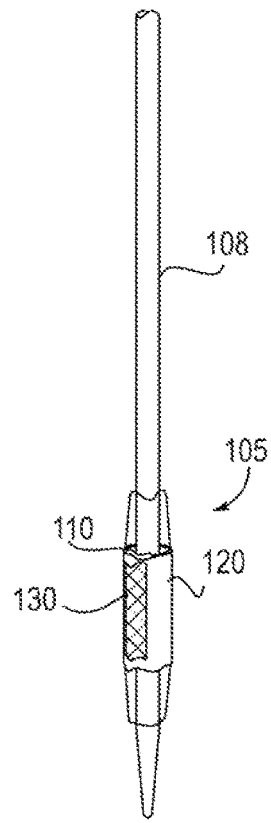
FIGS. 4A and 4B illustrate, respectively, perspective and top views of an unexpanded expandable support member.
Figure 4B:
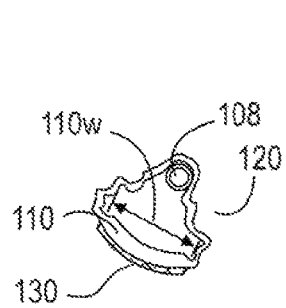

FIGS. 4A and 4B illustrate perspective and top views of an unexpanded expandable support member 105, respectively. In the unexpanded condition shown in FIGS. 4A and 4B, the surface area of the operative element 130 and the first portion 110 is greater than the surface area of the second portion 120. The expandable member first portion has a width 110$w$.

Figure 5A:
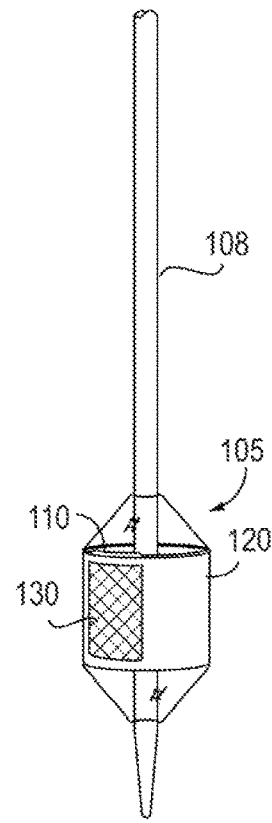
FIGS. 5A and 5B illustrate, respectively, perspective and top views of a partially expanded expandable support member.
Figure 5B:
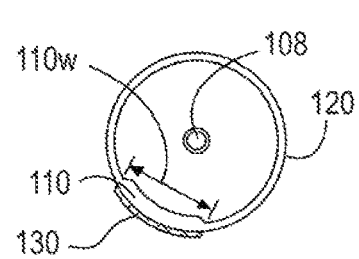

FIGS. 5A and 5B show perspective and top views, respectively, of a partially expanded expandable support member 105. In the partially expanded condition illustrated in FIGS. 5A and 5B, the surface area of the operative element 130 (a diagnostic or therapeutic instrument) and the first portion 110 is less than the surface area of the second portion 120.

Figure 6A:
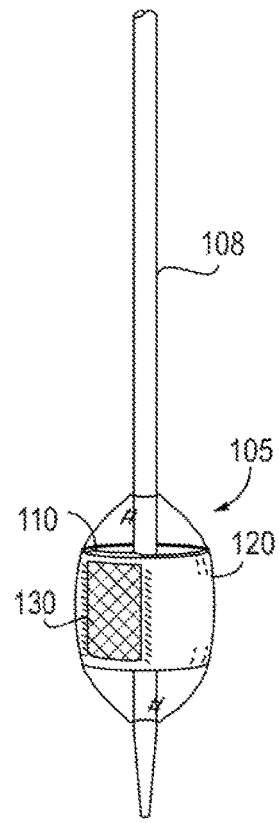
FIGS. 6A and 6B illustrate, respectively, perspective and top views of an expanded expandable support member.
Figure 6B:
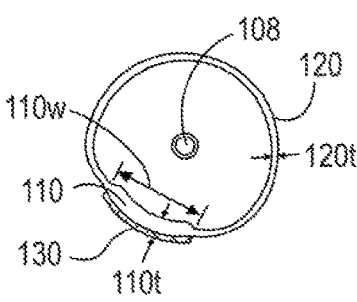

FIGS. 6A and 6B show perspective and top views, respectively, of an expanded expandable support member 105. In the partially expanded condition illustrated in FIGS. 6A and 6B, the surface area of the operative element 130 and the first portion 110 remains less than the surface area of the second portion 120. When the expandable support member is expanded as illustrated in FIGS. 6A, 6B, the surface area of the therapeutic or diagnostic element 130 is different that the surface area of the expandable element second portion 120. The same can be said for the unexpanded condition illustrated in FIGS. 4A, 4B. In the case of the expanded condition in FIGS. 6A and 6B, the second portion 120 is different because it has a greater surface area than the therapeutic or diagnostic instrument 130.

FIGS. 4A-6B also illustrate an embodiment of an expandable support member 105 where the expansion ratio of the expandable member second portion is greater than 1 and the expansion ratio of the expandable member first portion and the operative element 130 is about 1. As a result, the expandable support member first portion width 110$w$ remains the same in all three conditions: the unexpanded state illustrated in FIGS. 4A, 4B, the partially expanded state illustrated in FIGS. 5A, 5B and the expanded state illustrated in FIGS. 6A, 6B.

FIG. 6B also illustrates an embodiment of an expandable support member wherein the wall thickness of the expandable support member first portion 110 is greater than the wall thickness of the expandable support member second portion 120. As illustrated, the wall thickness 110$t$ is greater than the wall thickness 120$t$. While not bound by theory, it is generally considered that if compliant sheets are otherwise identical, a thinner sheet is more compliant, and has a greater expansion index in comparison to a thicker sheet. Thus, the thicker wall of the first portion 110 will resist expansion forces applied to the expandable support member, and the expansive forces will preferentially expand the more compliant thinner sidewalls of the second portion 120. In various respects, "preferentially" is to be understood as generally used in the art and refers to a desired, predetermined, or selected result. "Preferentially" may refer to designing for or controlling a process to achieve a desired result. For example, the expandable support member may be manufactured so the resulting production has a first portion with a desired predetermined expansion index. In various respects, "preferentially" and "selectively" or used somewhat interchangeably.

Figure 7:
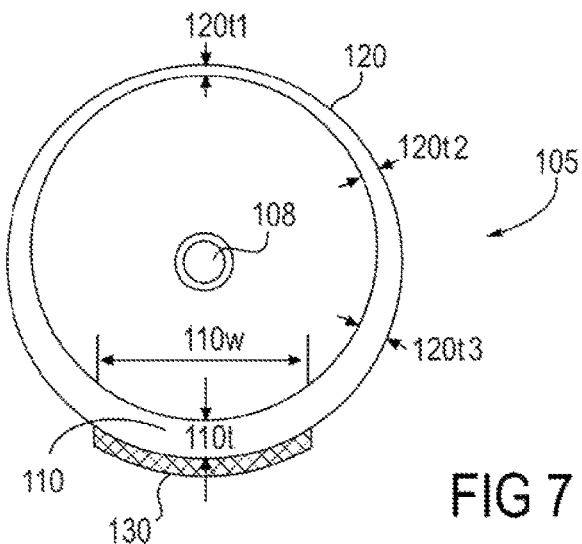
FIG. 7 illustrates a section view of an expandable support member with greater wall thickness in the first portion than in the second portion.

FIG. 7 provides a radial section view of an embodiment of an expandable support member 108 that has variable wall thickness as a whole, in circumferential terms encompassing both the first portion 110 and the second portion 120. More particularly, the first portion 110, as a whole, has a greater thickness 110$t$ than any circumferential region of the second portion 120. The second portion 120, as a whole, actually has a variable thickness, as shown, for example, at points 120$t$1, 120$t$2, and 120$t$3, where, in relative terms, 120$t$1 has the least thickness, 120$t$2 has an intermediate thickness, and 120$t$3 has the greatest thickness. The wall thickness 120$t$ of the second portion is shown as linearly or continuously increasing from 120$t$1 to 120$t$2 and then to 120$t$3, however, the wall thickness of the second portion may vary in non-linear or stepwise manner, or in any other manner suited to the expansion index desired for the expandable support member second portion.

Figure 8:
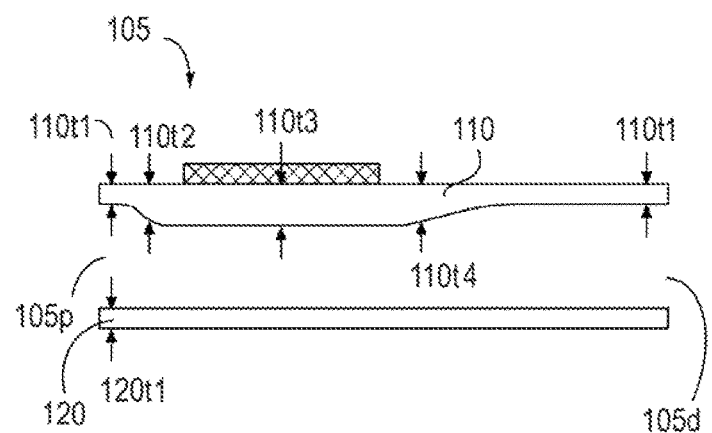
FIG. 8 illustrates a section view of an expandable support member with a variable wall thickness along the longitudinal axis of the expandable support member.

FIG. 8 provides a section view of a particular embodiment of a cylindrical expandable support member 105 and focuses on a variable wall thickness along the longitudinal axis of the expandable support member first portion 110. While the expandable support member second portion 120 and the operative element 130 are each shown as having a respective uniform thickness, there are alternative embodiments of the invention where the thickness of the expandable support member second portion 120 and the therapeutic or diagnostic instrument 130 may also be variable. FIG. 8 shows an expandable support member first portion having a thickness 110$t$1 at both the proximal end 105$p$ and the distal end 105$d$. Moving distally (or centrally, with respect to the first portion as a whole) from the proximal end 105$p$, the thickness increases from 110$t$1 to 110$t$2. Continuing to move distally in the vicinity of the operative element 130, the thickness increases from 110$t$2 to 110$t$3. Continuing to move distally beyond the vicinity of the operative element 130, the thickness decreases from 110$t$3 to 110$t$4. Moving still more distally from the vicinity of the operative element 130, the thickness decreases from 110$t$4 back to a thickness of 110$t$1. The transition from 110$t$1 through 110$t$2, to 110$t$3 is shown as having a step-wise nature, a type of thickness change mentioned above. An alternative embodiment, included in the invention, is one where such transitions are continuous or smooth.

Variable wall thicknesses and variable types of transition continuity between thicknesses may be used to tailor the expansion response of an expandable support member overall and the demarcation between expandable or distensible portions (e.g., a second portion) and substantially non-expandable or non-distensible portions (e.g., a first portion) of a member which is nevertheless expandable as a whole. These local variations, with distinct expansion ratios or indices of expansion, also can be understood as collectively determining the expandability of the expansion member as a whole (including constituent portions 1 and 2). It can further be understood that while the invention has been generally described and exemplified in figures as having a first portion, upon which an operative element is arranged, and a second portion that does not specifically contribute to the support of the operative element (such portion having a larger expansion index than the first portion) there may be more than one such "second" portion, as may be defined by having a larger expansion index than the first portion, and such embodiments are included within the scope of the invention. Merely by way of example, an expandable member may include a first portion with an expansion index of about 1, a second portion with an expansion index of about 1.4, and a third portion (a second "second" portion) with an expansion index of about 1.8 (i.e. 80% expansion).

Altering the wall thickness or other dimensions of expandable support member overall, the first or second expandable member portions or the operative element is the not only technique to vary an expansion index. One or more reinforcing elements on or within the expandable support structure first portion for this purpose. Moreover, in one aspect, the reinforcing elements are part of the therapeutic or diagnostic device.

Figure 9:
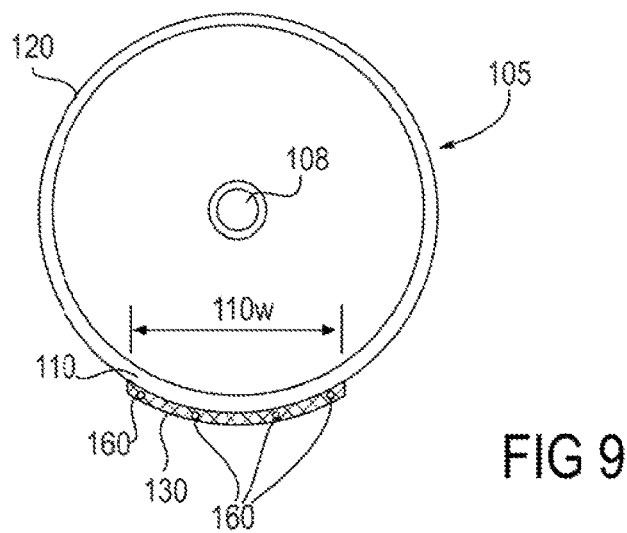
FIG. 9 illustrates a section view of an expandable support member where the reinforcing elements are part of the diagnostic or therapeutic device.

FIG. 9 provides a section view of an expandable support member 105 where the reinforcing elements 160 are part of the diagnostic or therapeutic device 130. In this embodiment, the wall thickness of the first portion 110 and second portion 120 of the expandable support member are different. In various embodiments, the wall thicknesses are the same. In various embodiments, the wall thickness of one or both is variable along its length or width. In this case, the average wall thickness of the first portion may be larger than the average wall thickness of the second portion.

In the exemplary embodiment, the variation in expansion response between the expandable support member first and second portions results from the restriction on expansion of the first portion caused by the dimension-stabilizing reinforcing elements associated with a device 130 that is attached to that portion. The reinforcing elements 160 may be rods integrated into the design of the diagnostic or therapeutic device 130. The reinforcing elements 160 may be continuous or segmented. As explained herein, the reinforcing elements may extend circumferentially less than 360 degrees, less than 180 degrees, or less than 90 degrees. In the embodiment shown in FIG. 9, the reinforcing elements 160 are aligned with the longitudinal axis of the expandable support member 105 and the operative element 130. The orientation of the reinforcing elements 160 may differ from the orientation illustrated depending upon the desired modification of the expansion response or resulting expansion index. The reinforcing elements 160 are sized and spaced appropriately so as not to interfere with the operation of the diagnostic or therapeutic device 130.

Figure 10A:
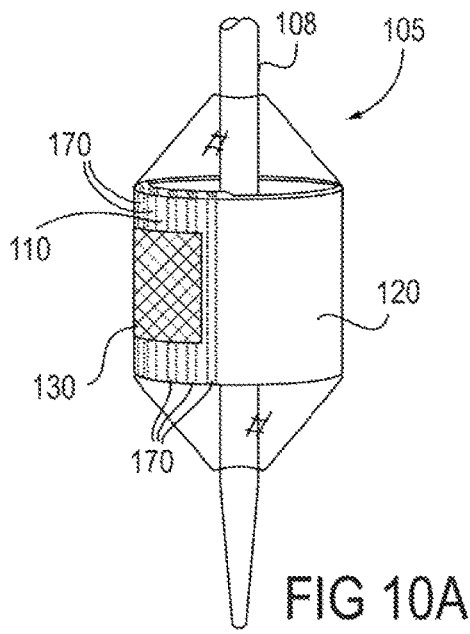
FIGS. 10A and 10B are perspective and section views, respectively, of an expandable support member first portion with one or more reinforcing elements.
Figure 10B:
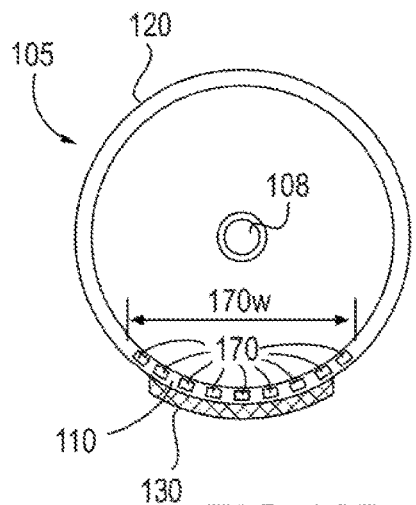

FIGS. 10A and 10B are perspective and radial cross sectional views, respectively, of an expandable support member first portion 110 with one or more reinforcing elements 170. The reinforcing elements 170 extend along the axial length of the expandable support member 105. The reinforced section of the first portion (110$w$, as seen in FIG. 9) is larger than the area of the instrument 130. The reinforcing elements 170 are embedded within the wall of the expandable support member first portion 110. The area occupied by the reinforcing elements 170 and the expandable support member first portion 110 is larger than the area of the operative element 130. In this embodiment, the wall thickness of the first portion 110 and second portion 120 of the expandable support member portions are the same. The variation in expansion response between the expandable support member first and second portions results from the restriction on expansion of the first portion caused by the reinforcement elements 170.

The reinforcing elements 170 are continuous rectangular pieces in this exemplary embodiment. Other shapes and sizes are feasible, depending upon the wall thickness of the first portion and the dimensions of the reinforcing elements. Suitable materials for the expandable support member include, but are not limited to, polymers and elastomers. Suitable materials for the reinforcing elements include, but are not limited to, metals such as stainless steel, nickel titanium, copper, or titanium; mesh wire; and polymers with low elasticity such as PEEK, ABS, or polyimide. In the embodiment shown in FIGS. 10A and 10B, the reinforcing elements 170 are aligned with the longitudinal axis of the expandable support member 105 and the operative element 130. The orientation of the reinforcing elements 170 may differ from the orientation illustrated depending upon the desired modification of the expansion response or resulting expansion index. The reinforcing elements 170 are sized and spaced appropriately so as not to interfere with the operation of the diagnostic or therapeutic device 130.

Figure 11:
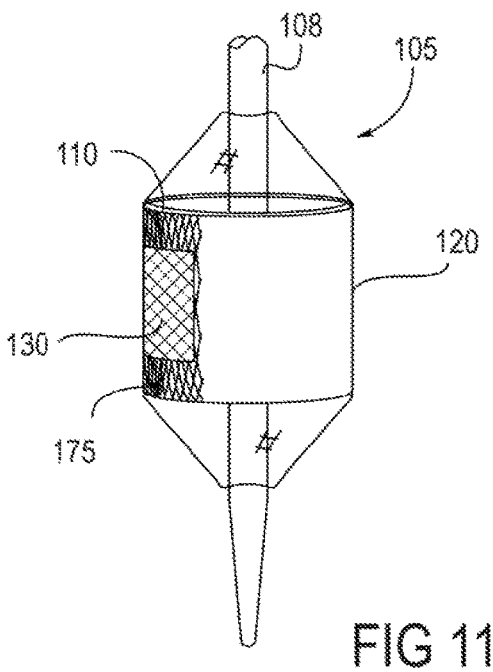
FIG. 11 illustrates a section view of an expandable support member first portion with a mesh reinforcing element.

FIG. 11 shows a section view of an expandable support member first portion 110 with a mesh reinforcing element 175. The mesh reinforcing element 175 may be positioned on a surface of the expandable support structure first portion 175, or be integrated or embedded into the surface. Alternatively, the mesh support element 175 may be more specifically associated with or integrated into the operative element 130 as described above with regard to FIG. 9. In another alternative embodiment, the mesh support element 175 may be positioned between the operative element 130 and the expandable support member 105.

Figure 12A:
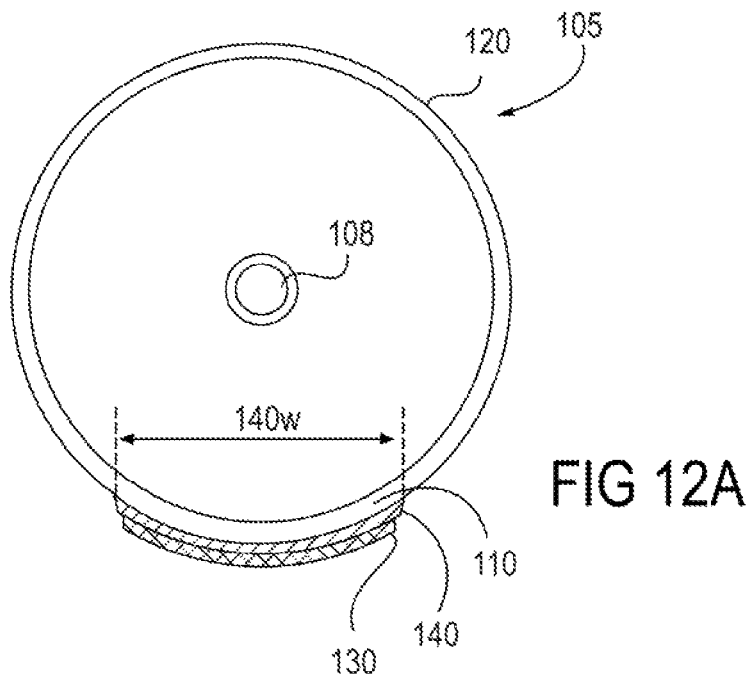
FIGS. 12A and 12B illustrate section views, respectively, of expandable support member first portions having one or more reinforcing elements on the expandable support member first portion or in the expandable support member first portion.
Figure 12B:
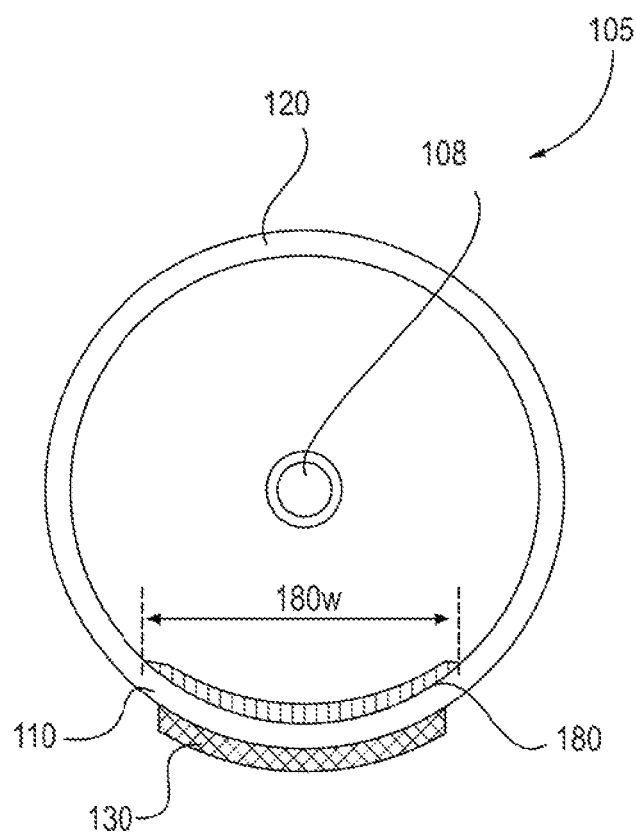

FIGS. 12A and 12B are radial cross section views, respectively, of expandable support member first portions 110 having one or more reinforcing elements arranged on either the interior or exterior surface of expandable member 105. FIG. 12A shows reinforcing element 140 on an exterior surface of portion 110, which by its position, separates the surface portion 110 from operative element 130. The width of the reinforced portion 140$w$ is greater than the width of operative element 130. Additionally, the area of the reinforced first portion is larger than the area of the operative element 130. In various embodiments, the surface area of the reinforced portion is larger than the operative element. In various embodiments, the surface area of the reinforced portion is smaller than the operative element. In various embodiments, the reinforced portion overlaps the operative element completely or partially. In various embodiments, the operative element overlaps the reinforced portion completely or partially.

The reinforcing element 140 may be a continuous or segmented structure. For example, the reinforcing element 140 may be of similar construction to the reinforced portions of the expandable support member first portions illustrated and described with regard to FIGS. 9, 10A, 10B, and 11. In some embodiments, the reinforced portion 140 of FIG. 12A may be a non-distensible electrode array backing comprising polyimide, as described further below.

FIG. 12B illustrates an expandable support member 105 having a reinforcing element 180 in the interior of the first portion 110 of the expandable support member. In this embodiment, the surface of expandable support member first portion 110 separates the therapeutic or diagnostic instrument 130 from the reinforcing element 180. The width of the reinforced portion 180$w$ is greater than the width of operative element 130. Additionally, the area of the reinforced first portion is larger than the area of the therapeutic or diagnostic element 130. The reinforcing element 180 may be a continuous or segmented structure. For example, the reinforcing element 180 may be of similar construction to the reinforced portions of the expandable support member first portions illustrated and described with regard to FIGS. 9, 10A, 10B, and 11.

In some embodiments, the reinforced portion 140 of FIG. 12A may be a flexible but non-distensible electrode array backing comprising a polymeric material. For example, the support 140 may comprise of a thin, rectangular sheet of polymer materials such as polyimide, polyester or other flexible thermoplastic or thermosetting polymer film. The support 140 may also comprise polymer covered materials, or other nonconductive materials. Additionally, the backing may include an electrically insulating polymer, with an electro-conductive material, such as copper, deposited onto a surface so that an electrode pattern can be etched into the material to create an array of electrodes.

Figure 13A:
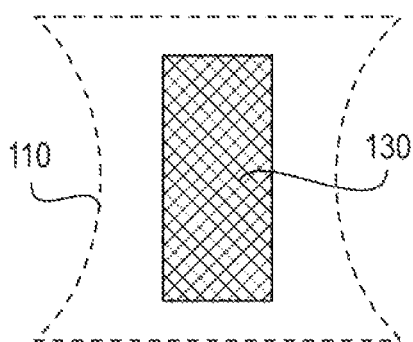
FIGS. 13A, 13B, and 13C illustrate various shapes of an expandable support member first portion.
Figure 13B:
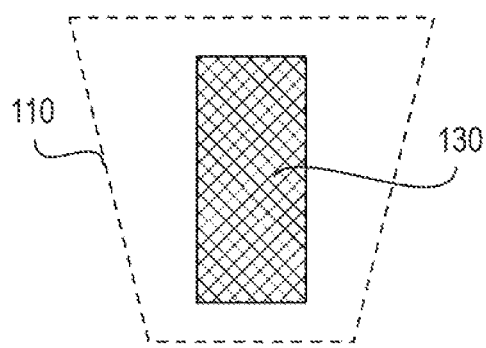
Figure 13C:
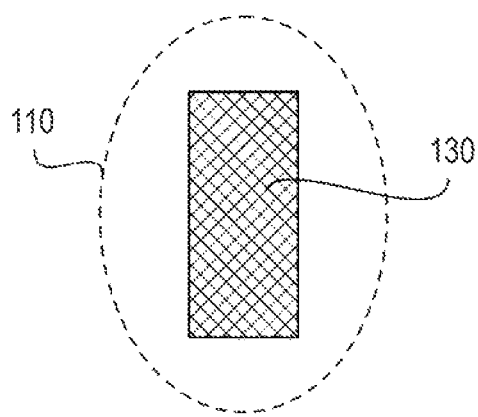

FIGS. 13A, 13B, and 13C show various shapes of an expandable support member first portion 110 embodiments. The size and shape of the operative element 130 and the expandable support member first portion 110 may be comparable as in the embodiments illustrated in FIGS. 2A-6B. The sizes may be comparable but the area of expandable support member first portion 110 may be larger than the area of the operative element 130 as illustrated in the embodiments of FIGS. 7, 8, 10A, 10B, and 11. The size and shape between the expandable support member first portion 110 and the operative element 130 may also be different. FIG. 13A shows a generally rectangular shaped operative element 130 on an hour glass-shaped expandable support member first portion 110. FIG. 13B shows a generally rectangular-shaped therapeutic or diagnostic device 130 on a trapezoidal-shaped expandable support member first portion 110. FIG. 13C shows a generally rectangular-shaped therapeutic or diagnostic device 130 on an oval shaped expandable support member first portion 110. In each of the previous examples, the operative element 130 maintains a generally rectangular shape while the size and shape of the expandable support member first portion 110 varies. It is to be appreciated that in some embodiments, the expandable support member first portion 110 maintains a generally rectangular shape while the size and shape of the operative element 130 is varied.

In various embodiments, the expandable support member is substantially tubular along the one or more second portions. The expandable support may be curviplanar with the first portion having a first radius and the one or more second portions having one or more radii different than the first radius. Although described above in terms of a partially tubular shape, one will appreciate that the expandable support member may have a variety of shapes in the expanded and unexpanded states including, but not limited to, polygons and complex shapes. In various embodiments, the expandable support member is substantially spiral shaped. The support member may be furled around an expansion member, such as a balloon, such that the expansion member unfurls the support member. Exemplars of furled expandable support members are disclosed in U.S. Pat. Nos. 7,150,145 and 7,344,535, incorporated herein for all purposes by this reference. The expandable support member may be configured with a first portion and at least a second portion as will be understood from the description herein. As the expandable support member unfurls, a section corresponding to the second portion expands differently than another section corresponding to the first portion.

Embodiments of the invention also include methods of fabricating expandable members, such as a balloon, with regions of varied thickness and with regions of varied composition. Typical methods of fabricating balloons include dip molding, whereby a mandrel of the desired final form of the balloon is dipped one or more times into a liquid polymeric solution that coats the mandrel and dries as a film. With multiple dippings into varied polymeric compositions, different compositions can be applied to a single balloon. By applying reinforcing elements to the mandrel before dipping, or between multiple dippings, reinforcing elements can be integrated into the balloon skin. By multiple dippings that selectively expose particular regions of the mandrel, such regions can be made selectively thicker, or have varied composition. By selectively masking regions of the mandrel during a dipping, regions of the balloon being fabricated can lack elements or compositions found elsewhere within the balloon skin.

In various embodiments, one or more of the expandable members are fabricated using a blow molding process. In various embodiments, the balloon is formed using blow molding and dipping in baths. In accordance with the above techniques for providing selective reinforcement, the tubing used to blow the balloon can begin with variations in wall thickness or contain support structures embedded in the tubing wall which are then translated to the blown balloon. In various embodiments, the blow molding process parameters including, but not limited to pull speed, heater dwell time, and heater nozzle design are adjusted to vary the wall thickness along the balloon length or circumferentially.

Embodiments of the expandable support member may also be used in methods of providing therapy to tissue in a body. The method includes positioning an instrument in proximity to tissue in a body selected to receive therapy. The instrument is supported by an expandable support member adapted for non-uniform expansion between a first portion and a second portion. Non-uniform expansion between a first portion and a second portion refers to the relative distribution of the expansion of the expandable support member between these different portions of the expandable support member. The expandable support member has been modified and configured such that, when exposed to expansion forces, the expandable support member response is not uniform across the entirety of the expandable support member. The first portion supports at least part of the instrument. Next, the expandable support member second portion is expanded until the instrument is in a therapeutic position relative to the tissue in a body selected to receive therapy. Next, therapy is provided to tissue selected to receive therapy using the instrument. In the case of a diagnostic instrument, the diagnostic process is carried out in the therapeutic position.

The therapeutic position will depend upon a number of factors. Among these factors are the types of tissue being treated, diagnosed or evaluated; the location of the tissue being treated, diagnosed, or evaluated; the design or type of therapeutic instrument employed; and the design or type of diagnostic instrument employed. In one aspect, the therapeutic position is a position where the instrument is in contact with a surface of the tissue selected to receive therapy. In another aspect, the therapeutic position is a position where the instrument is spaced apart from the tissue targeted to receive therapy.

The methods of providing therapy may also vary according to the specific therapy being performed. For example, the method may include providing therapy to tissue selected to receive therapy using the instrument by ablating some of the tissue selected to receive therapy. Alternatively, the method may include evaluation or information gathering steps prior to, in conjunction with or after performing other acts with a therapeutic instrument. In one aspect, the therapy may include providing therapy to tissue selected to receive therapy using the instrument by obtaining information about some of the tissue selected to receive therapy.

Figure 14A:
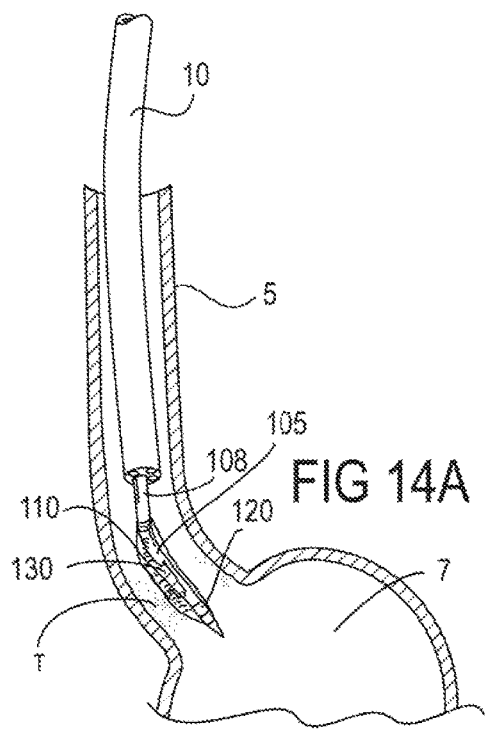
FIG. 14A illustrates an instrument supported by an unexpanded expandable support member.
Figure 14B:
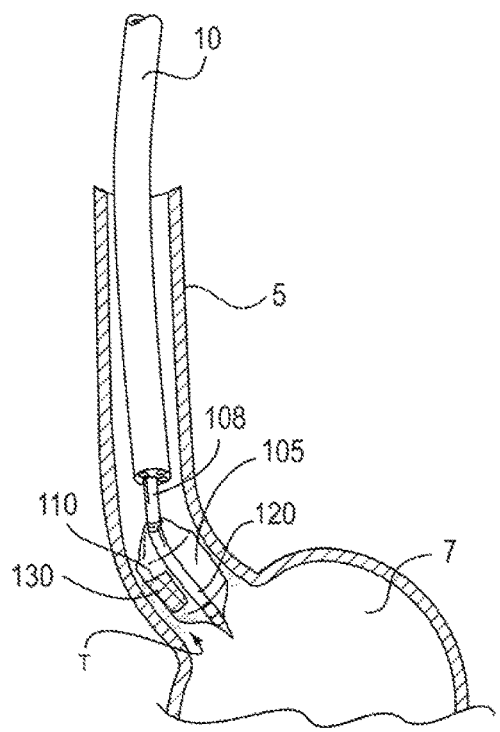
FIG. 14B illustrates an instrument supported by expandable support member as in FIG. 14A where the support member is partially expanded.
Figure 14C:
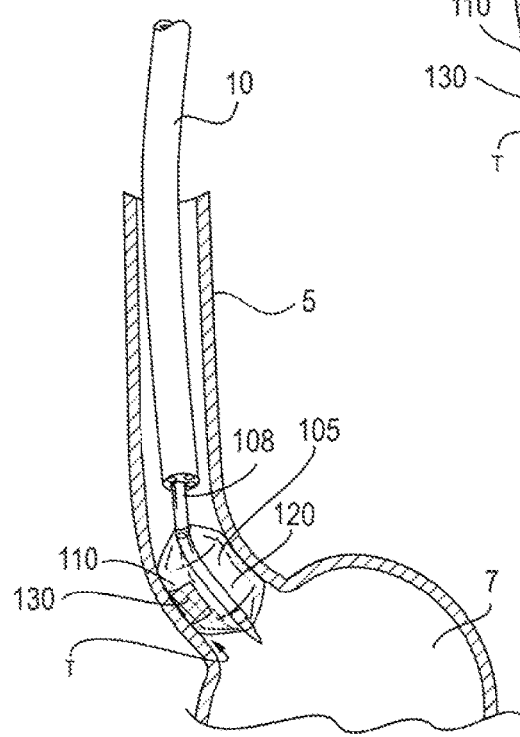
FIG. 14C illustrates an instrument supported by an expandable support member as in FIG. 14A where the expandable support member is expanded.

FIGS. 14A-14C show the positioning and use of an instrument supported by an expandable support member. In this illustrative embodiment, the instrument is used to provide therapy to a target tissue site (T) selected for therapy within a portion of the human esophagus 5, and is delivered by way of an endoscope. FIG. 14A shows an operative element, such as an ablational structure 130 supported by an unexpanded expandable support member 105. An endoscope 10 has been advanced into position within the esophagus 5 above the stomach 7. From this position within the esophagus 5, the unexpanded expandable support member 105 is advanced through a working channel of endoscope 10. The position of the unexpanded expandable support member 105 is adjusted to place the instrument 130 in position relative to the tissue (T) selected to receive therapy.

FIG. 14B shows an instrument 130 supported by expandable support member 105 as in FIG. 14A where the support member 105 is partially expanded. FIG. 14C shows an operative element 130 supported by an expandable support member 105 as in FIGS. 14A and 14B where the expandable support member 105 is fully expanded. In this position, the instrument 130 is in a position to provide therapy to the target tissue site (T) selected to receive therapy. By such full or appropriate degree of expansion of the expandable member, a "therapeutic contact", or "therapeutically effective contact" between the ablation structure 101 and the targeted tissue is achieved. Such therapeutic contact generally refers to complete or substantially-complete contact between all or a portion of a target site on the tissue surface (e.g. a site on the wall of a luminal organ of the gastrointestinal tract) by all or a substantial portion of the ablating surface of ablation structure 130.

FIGS. 14A-14C show the use of an expandable support member in conjunction with an endoscope. However, the use of expandable support member embodiments of the invention is not so limited; it may be positioned for use to provide therapy or diagnosis using any of a number of techniques. For example, the expandable support member may be mounted on a catheter and introduced directly into the lumen. Still further, the catheter based embodiment may be used alone or in parallel with another device, such as an endoscope, placed in the lumen. The catheter based expandable support member could be operated independently of the endoscope, mounted onto the endoscope, or configured to pass through the working channel of the endoscope (FIGS. 14A-14C).

Embodiments of the expandable support member 105 of the present invention may be used for providing therapy or diagnosis of body lumens, hollow body organs, or cavities within the body. The dimensions of the expandable support member 105 may be modified or the expansion response may be adjusted depending upon the specific anatomical site selected for therapy. In particular, the dimensions or operational characteristics of the therapeutic or diagnostic instrument may require the instrument to be of a specific size, formed of a particular composition, or placed in a certain position on the expandable instrument or relative to the tissue selected to receive therapy. Consequently, the placement of an operative element such as an ablational structure on the expandable support member may rely on the expansive characteristics of the expandable support member to move the instrument into the desired position to provide therapy. From these various considerations, the ratio of the sizes of the expandable support member first portion to the second portion and between the portions and the instrument may be designed to differ, depending upon the intended use of the instrument. Additionally, the expansion characteristics, including the expansion ratio of the expandable support member first and second portions may also vary depending upon the specific application and anatomical site of interest.

The examples below illustrate how the difference in size and operation of the expandable support member may be used to accommodate differences in an anatomical site. The anatomical site considered in these examples is the human esophagus. The difference in the size of the esophagus to be treated may result in situations where the second portion of expandable support member is smaller than the first portion of the expandable support member even when the expandable member is expanded (the substantial majority of expansion coming from the second portion). In other circumstances, typically in larger lumen sizes, the first portion of the expandable support member may be larger than the second portion of the expandable support member when the second portion is non-expanded. However, when the expansion member is expanded, the second portion (largely responsible for expansion as a whole) is expanded, it may become larger than the first portion.

One factor that leads to this result is that the expandable support member first portion and the accompanying operative element are typically optimized to provide therapy or to diagnose an optimal size of the lumen surface to allow for use in a large patient population. When the expandable support member is expanded, the surface area of the operative element is different that the surface area of the expandable support member second portion. In one aspect, the difference in surface area may result in the surface area of the operative element being larger than the expandable support member second portion. In another aspect, the difference in surface area may result in the surface area of the operative element being smaller than the expandable support member second portion. As a result, the anatomical variation in the size of the lumen is compensated for by the second portion of the expandable support member. The use of the second portion to accommodate variations in lumen size is illustrated in the following examples.

EXAMPLE 1

The exemplary body lumen has circumference of about a 60 mm. A device (such as an ablational structure) encompassing an arc or a circumferential span of 40 mm arc is mounted on a comparably sized first portion of an expandable support member. In this example, when the 40 mm device is in position to provide therapy, the expandable support member second portion would be expanded to fill out the remaining 20 mm in lumen circumference. Thus, when the expandable support member is positioned for use in the lumen and the second portion of the expandable support member is expanded, the second portion has a smaller area than the first portion.

EXAMPLE 2

The exemplary body lumen has a circumference of about 120 mm. A device such as an ablational structure encompassing an arc or a circumferential span of 40 mm is mounted on a comparably sized expandable support member first portion. Prior to positioning the device for use, the expandable support member second portion has a smaller area than the expandable support member first portion. However, when the expandable support member is expanded and is in position for use, the expandable support member second portion would be expanded to cover the remaining 80 mm in lumen circumference. Thus, when the expandable support member is positioned for use in the lumen and the second portion is expanded, the expandable support member second portion has a larger area than the expandable support member first portion.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A medical device, comprising:
   an expandable support member having a first portion and a second portion, wherein the first portion is arranged such that it occupies an arc orthogonal to a longitudinal axis of the expandable support member and extends less than a full length along the longitudinal axis of the expandable support member, the first portion of the expandable support member having an exterior surface with a first surface area;
   an expansion-resistant reinforcing element having a first side with a second surface area and a second side opposite the first side, the second surface area being substantially the same as the first surface area, the entire first side fixedly coupled with the exterior surface of the first portion of the expandable support member, wherein expansion of the first portion is constrained by at least the expansion-resistant reinforcing element such that the first portion has a smaller expansion index than that of the second portion; and
   an operative element fixedly coupled with the second side of the expansion-resistant reinforcing element, wherein the operative element is operative over a third surface area that is substantially the same as the first surface area.

2. The device of claim 1, wherein the first and second portions are curviplanar aspects of the expandable support member, the first portion being partially-circumferential around the expandable support member.

3. The device of claim 1, wherein the operative element comprises a therapeutic instrument.

4. The device of claim 3, wherein the therapeutic instrument comprises a member selected from the group consisting of a bipolar radiofrequency (RF) electrode array, RF monopolar electrodes, and a combination of the same.

5. The device of claim 3, wherein the therapeutic instrument is an ablation device adapted to delivery energy to tissue, the ablation device selected from the group consisting of an RF ablation device, a microwave ablation device, an ultrasonic ablation device, a resistive heating ablation device, a chemical ablation device, a cryogenic ablation device, an ablation device for delivering a heatable fluid, and an optical heatable fluid.

6. The device of claim 1, wherein the expansion index of the expandable support member first portion is about 1.

7. The device of claim 1, wherein the expansion index of the expandable support member first portion is less than about 1.1.

8. The device of claim 1, wherein the expansion index of the expandable support member second portion is greater than 1 and less than 10.

9. The device of claim 1, wherein the expansion index of the expandable support member second portion is between about 2 and about 10.

10. The device of claim 1, wherein the expansion index of the second portion of the expandable support member relates to expansion along the longitudinal axis of the expandable support member.

11. The device of claim 10, wherein the expansion index of the second portion of the expandable support member further relates to expansion along a second axis orthogonal to the longitudinal axis of the expandable support member.

12. The device of claim 1, wherein the surface area of the operative element is different than the surface area of the expandable support member second portion when the expandable support member is expanded.

13. The device of claim 1, wherein the expansion-resistant reinforcing element comprises a flexible, non-distensible polymeric support.

14. The device of claim 13, wherein the flexible, non-distensible polymeric support comprises polyimide.

15. The device of claim 1, wherein the expandable support member comprises a balloon.

16. The device of claim 1, wherein the expandable support member is substantially cylindrical.

17. The device of claim 1, further comprising an elongate member adapted to support the expandable support member at a distal portion of the elongate member.

18. The device of claim 17, wherein the elongate member has a central longitudinal axis, and wherein the expandable support member is substantially cylindrical and coupled with the elongate member such that the central longitudinal axis of the elongate member and the longitudinal axis of the expandable support member are coaxial.

19. The device of claim 17, wherein the expandable support member is circumferentially arranged around the distal portion of the elongate member.

20. The device of claim 17, wherein at least a portion of the elongate member extends through a complete length of the expandable support member.

21. The device of claim 20, wherein at least a portion of the elongate member extends distally beyond the expandable support member.

22. A medical device, comprising:
   an expandable support member adapted for coupling to a distal portion of an elongate member, the expandable support member having a first curviplanar portion and a second curviplanar portion, wherein the first curviplanar portion is arranged such that it occupies an arc orthogonal to a longitudinal axis of the expandable support member and extends less than a full length along the longitudinal axis of the expandable support member, the first curviplanar portion of the expandable support member having an exterior surface with a first surface area;
   an expansion-resistant reinforcing element having a first side with a second surface area and a second side opposite the first side, the second surface area being substantially the same as the first surface area, the entire first side fixedly coupled with the exterior surface of the first curviplanar portion of the expandable support member, wherein expansion of the first curviplanar portion is constrained by at least the expansion-resistant reinforcing element such that the first curviplanar portion and the second curviplanar portion of the expandable support member have different expansion indices; and an operative element fixedly coupled with the second side of the expansion-resistant reinforcing element, wherein the operative element is operative over a third surface area that is substantially the same as the first surface area.

23. The device of claim 22, wherein the first curviplanar portion and the second curviplanar portion are adapted such that a majority of the expansion occurs in the second curviplanar portion.

24. The device of claim 22, wherein the device is substantially round in an expanded state and the operative element extends less than 360 degrees around the device.

25. A system for ablation of tissue at a target site in an esophagus, comprising:
an expandable member adapted for coupling to a distal portion of an elongate member and sized to be positionable and expandable in the esophagus; and
an radio frequency (RF) ablation element having a first side with a first surface area and the entire first side fixedly coupled with an exterior surface of a first partially-circumferential portion of the expandable member, wherein the first partially-circumferential portion is arranged orthogonal to a longitudinal axis of the expandable member and extends less than a full length along the longitudinal axis of the expandable member, and wherein the first surface area is substantially the same as a surface area of the exterior surface of the first partially-circumferential portion, the RF ablation element adapted to resist expansion of the first partially-circumferential portion, the RF ablation element comprising a plurality of RF electrode pairs, a width of each RF electrode and a spacing between adjacent RF electrodes selected to allow depth-controlled ablation at the target site.

26. A medical device for ablation of tissue at a target site in an esophagus, comprising:
an expandable member adapted for coupling to a distal portion of an elongate member and sized to be positionable and expandable in the esophagus;
an electrode support comprising a flexible, non-distensible backing and having a first side with a first surface area and a second side opposite the first side, the entire first side of the electrode support fixedly coupled with a partially-circumferential exterior surface of the expandable member such that expansion of the partially-circumferential exterior surface is resisted by at least the electrode support, wherein the partially-circumferential exterior surface has a second surface area and occupies an arc orthogonal to a longitudinal axis of the expandable member and extends less than a full length along the longitudinal axis of the expandable member, and wherein the first surface area is substantially the same as the second surface area; and
a plurality of radio frequency (RF) electrode pairs on the second side of the electrode support, a width of each RF electrode and a spacing between adjacent RF electrodes selected to allow depth-controlled ablation at the target site.

27. A method of providing therapy to tissue in a body, comprising:
positioning a device comprising:
an expandable support member having a first portion and a second portion, wherein the first portion is arranged such that it occupies an arc orthogonal to a longitudinal axis of the expandable support member and extends less than a full length along the longitudinal axis of the expandable support member, the first portion of the expandable support member having an exterior surface with a first surface area;
an expansion-resistant reinforcing element having a first side with a second surface area and a second side opposite the first side, the second surface area being substantially the same as the first surface area, the entire first side fixedly coupled with the exterior surface of the first portion of the expandable support member, wherein expansion of the first portion is constrained by at least the expansion-resistant reinforcing element; and
an operative element fixedly coupled with the second side of the expansion-resistant reinforcing element, wherein the operative element is operative over a third surface area that is substantially the same as the first surface area;
expanding the second portion of the expandable support member to place the operative element in an operating position adjacent to tissue at the target site; and
providing therapy to the target tissue site using the operative element.

28. The method of claim 27, further comprising expanding the first portion to place the operative element in the operating position, wherein the first portion is expanded less than the second portion.

29. The method of claim 27, wherein the first portion is expanded by less than 10% and the second portion is expanded by more than 200%.

30. The method of claim 27, wherein the operating position is where the operative element is in contact with the target tissue site.

31. The method of claim 27, wherein providing therapy to the target tissue site using the operative element comprises ablating at least a portion of the tissue at the target site.

32. The method of claim 27, wherein providing therapy to the target tissue site using the operative element comprises obtaining information related to the tissue selected to receive therapy.

33. A method for treating tissue in a luminal organ, the method comprising:
inserting an electrode deployment apparatus into the luminal organ, the electrode deployment apparatus comprising:
an expandable member;
an electrode support comprising a flexible, non-distensible backing and having a first side with a first surface area and a second side opposite the first side, the entire first side of the electrode support fixedly coupled with a partially-circumferential exterior surface of the expandable member such that expansion of the partially-circumferential exterior surface is resisted by at least the electrode support, wherein the partially-circumferential exterior surface has a second surface area and occupies an arc orthogonal to a longitudinal axis of the expandable member and extends less than a full length along the longitudinal axis of the expandable member, and wherein the first surface area is substantially the same as the second surface area; and
an array of electrodes arranged on the second side of the electrode support;
expanding the expandable member to engage the electrodes with a target site on a wall of the luminal organ while maintaining an electrode density of the engaged electrodes; and
delivering energy from the electrodes to the target site.

* * * * *